US007351414B2

(12) United States Patent
Gaich et al.

(10) Patent No.: US 7,351,414 B2
(45) Date of Patent: *Apr. 1, 2008

(54) METHOD OF REDUCING THE RISK OF BONE FRACTURE

(75) Inventors: Gregory A. Gaich, Indianapolis, IN (US); Willard H. Dere, Westlake Village Ventura, CA (US); Janet M. Hock, Indianapolis, IN (US)

(73) Assignee: Eli Lilly and Company, Indianapolis, IN (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/684,996

(22) Filed: Mar. 12, 2007

(65) Prior Publication Data

US 2007/0161567 A1    Jul. 12, 2007

Related U.S. Application Data

(63) Continuation of application No. 11/098,909, filed on Apr. 5, 2005, now abandoned, which is a continuation of application No. 10/443,693, filed on May 22, 2003, now abandoned, which is a continuation of application No. 09/647,278, filed as application No. PCT/US99/18961 on Aug. 19, 1999, now Pat. No. 6,977,077.

(60) Provisional application No. 60/097,151, filed on Aug. 19, 1998, provisional application No. 60/099,746, filed on Sep. 10, 1998.

(51) Int. Cl.
*A61K 38/29* (2006.01)
*C07K 14/635* (2006.01)

(52) U.S. Cl. ................ 424/198.1; 514/12; 530/324

(58) Field of Classification Search .................. None
See application file for complete search history.

(56) References Cited

U.S. PATENT DOCUMENTS

| 4,086,196 | A | 4/1978 | Tregear |
| 4,698,328 | A | 10/1987 | Neer et al. |
| 5,510,370 | A | 4/1996 | Hock |
| 6,258,778 | B1 | 7/2001 | Rodgers et al. |
| 6,569,442 | B2 | 5/2003 | Gan et al. |
| 6,770,623 | B1 | 8/2004 | Chang et al. |
| 6,977,077 | B1* | 12/2005 | Hock et al. ............ 424/198.1 |
| 7,144,861 | B2 | 12/2006 | Chang et al. |
| 7,163,684 | B2* | 1/2007 | Gaich et al. ............ 424/198.1 |
| 2006/0094642 | A1 | 5/2006 | Gaich et al. |

FOREIGN PATENT DOCUMENTS

| EP | 0 497 915 | 4/1995 |
| EP | 1 059 933 B1 | 1/2003 |
| JP | 08073376 | 3/1996 |
| JP | 08310965 | 11/1996 |
| WO | WO 96/35422 | 11/1996 |
| WO | WO 98/14478 | 4/1998 |
| WO | WO 99/12561 | 3/1999 |
| WO | WO 01/22093 A1 | 3/2001 |

OTHER PUBLICATIONS

U.S. Appl. No. 10/443,693, filed May 22, 2003, Hock et al.
U.S. Appl. No. 11/541,862, filed Oct. 2, 2006, Chang, et al.
U.S. Appl. No. 11/541,863, filed Oct. 2, 2006, Chang, et al.
Andreassen, TT, et al., "In Old Rats Intermittent Parathyroid Hormone (1-34) Treatment Increases Callus Formation and Mechanical Strength of Healing Fractures," *Department of Connective Tissue Biology*, University of Aarhus, Denmark, ASBMR 21$^{st}$ Annual Meeting, S417.
Boyce, RW, et al., "Effects of Intermittent hPTH(1-34) Alone and in Combination with 1,25(OH)$_2$D$_3$ or Risedronate on Endosteal Bone Remodeling in Canine Cancellous and Cortical Bone," *Journal of Bone and Mineral Research*, vol. 11, No. 5, pp. 600-613, (1996).
Chapuy, M, et al., "Vitamin D$_3$ and Calcium to Prevent Hip Fractures in Elderly Women," *The New England Journal of Medicine*, vol. 327, No. 23, pp. 1637-1641, (1992).
Chapuy, MC, et al., "Biochemical effects of calcium and vitamin D supplementation in elderly, institutionalized, vitamine D-deficient patients," *Rev Rhum Engl Ed*, vol. 63, No. 2, pp. 135-140, (Feb. 1996).
Clinical Investigator's Brochure dated Jun. 30, 1995.
Clinical Study Main Report: Safety and Pharmacological Effects of LY333334 on Biochemical Markers of Bone Metabolism in Healthy, Postmenopausal Women.
Conference Report, "Consensus Development Conference: Diagnosis, Proohylaxis, and Treatment of Osteoporosis," *The American Journal of Medicine*, vol. 94, pp. 646-650, (Jun. 1993).
Cosman, F, et al., "Estrogen Protection Against Bone Resorbing Effects of Parathyroid Hormone Infusion," *Annals of Internal Medicine*, vol. 118, No. 5, 337-343 (1993).
Cosman, F, et al., "Is Parathyroid Hormone a Therapeutic Option for Osteoporosis? A Review of the Clinical Evidence," *Calcified Tissue International*, vol. 62, 475-480 (1998).
Dawson-Hughes, B, et al., "Effect of Calcium and Vitamin D Supplementation on Bone Density in Men and Women 65 years of age or Older," *New England Journal of Medicine*, vol. 337, No. 10, 1197, pp. 670-676, (Sep. 4, 1997).
Delmas, PD, "Treatment of postmenopausal osteoporosis," *The Lancet*, vol. 359, pp. 2018-2026, (Jun. 8, 2002).

(Continued)

Primary Examiner—Ruixiang Li
(74) Attorney, Agent, or Firm—MaryAnn Wiskerchen

(57) ABSTRACT

The invention relates to a method for increasing the toughness and/or stiffness of bone and/or reducing the likelihood and/or severity of bone fracture by administering a parathyroid hormone. The method can be employed to increase toughness or stiffness of bone at a site of a potential or actual trauma, such as the hip or spine of a person at risk of or suffering from osteoporosis. The method of the invention can reduce the incidence of vertebral fracture, reduce the incidence of multiple vertebral fractures, reduce the severity of vertebral fractur and/or reduce the incidence of nonvertebral fracture.

4 Claims, 10 Drawing Sheets

OTHER PUBLICATIONS

Dempster, DW, et al., "Anabolic Actions of Parathyroid Hormone on Bone," *Endocrine Reviews*, vol. 14, No. 6, 690-709 (1993).

Ejerstad, C, et al., "Human Parathyroid Hormone (134) and (184) Increase the mechanical Strength and Thickness of Cortical Bone in Rats," *Journal of Bone and Mineral Research*, vol. 3, No. 9, 1097-1101 (1993).

Finkelstein, JS, et al., "Increases in bone density after discontinuation of long-term GnRH analog and PTH administration in women with endometriosis," *Journal of Bone and Mineral Research*, vol. 23, Supplement No. 5, F459 Abstract, S518 (1998).

Finkelstein, JS, et al., "Increases in Bone Mineral Density after Discontinuation of Daily Human Parathyroid Hormone and Gonadotriopin-Releasing Hormone Analog Administration in Women with Endometriosis," *The Journal of clinical Endocrinology & Metabolism*, vol. 84, No. 4, 1214-1219 (1999).

Finkelstein, JS, et al., "Parathyroid Hormone for the Prevention of Bone Loss Induced by Estrogen Deficiency," *The New England Journal of Medicine*, vol. 331, No. 24, 1618-1623 (1994).

Finkelstein, JS, et al., "Prevention of Estrogen Deficiency-Related Bone Loss With Human Parathyroid Hormone-(1-34)," *JAMA*, Vo.. 280, No. 12, 1067-1073 (1998).

Fraser, DR, B.E.C. Nordin (Ed.), Calcium-Regulating Hormones: Vitamin D, Chapter 2, pp. 27-41.

Fujita, T, et al., "Parathyroid Hormone in the Treatment of Osteoporosis," *BioDrugs*, vol. 15, No. 1, pp. 721-728, (2001).

Fujita, T, et al., "Effect of an Intermittent Weekly dose of Human Parathyroid Hormone (1-34) on Osteoporosis: A Randomized Double-masked Prospective Study Using Three Dose Levels," *Osteoporosis International*, vol. 9, 296-306 (1999).

Fukunaga, M, et al., "Effect of a Small Dose of Human Parathyroid Hormone (1-34) on Bone Mass in the Lumbar Vertebrae in Patients with Senile Osteoporosis," pp. 3371-3382, (1997).

Hesch, RD, et al., "Increase of Vertebral Density by Combination Therapy with Pulsatile 1-38hPTH and Sequential Addition of Cacitonin Nasal Spray in Osteoporotic Patients," *Calcified Tissue International*, Vo. 44, 176-180 (1989).

Hesch, RD, et al., "Results of a Stimulatory Therapy of Low Bone Metabolism in Osteoporosis with (1-38) hPTH and Diphosphonate EHDP," *Klinische Wochen Shrift*, vol. 66, 976-984 (1988).

Hesp, R, et al., "The Relationship Between Changes in Femoral Bone Density and Calcium Balance in Patents with Involutional Osteoporosis Treated with Human Parathyroid Hormone Fragment (hPTH 1034)," *Metabolic Bone Disease & Related Research*, vol. 2, 331-334 (1981).

Hirano T, et al., "Anabolic Effects of Human Biosynthetic Parathyroid Hormone Fragment (1034), LY333334, on Remodeling and Mechanical Properties of Cortical Bone in Rabbits," *Journal of bone and Mineral Research*, vol. 14, No. 4, 536-545 (1999).

Hodsman, AB, et al., "A Randomized Controlled Trial to Compare the Efficacy of Cyclical Parathyroid Hormone Versus Cyclical Parathyroid Hormone and Sequential Cacitonin to Improve Bone Mass in Postmenopausal Women with Osteoporosis," *Journal of Clinical Endocrinology and Metabolism*, vol. 82, No. 2, 620-628 (1997).

Hodsman, AB, et al., "Parathyroid Hormone: The Clinical Experience and Prospects," Chapter 4, 83-108 (1998).

Holzer, G, et al., "Parathyroid Hormone Enhances Fracture Healing", Clinical Orthopaedics and Related Research, No. 366, pp. 258-263 (1999).

Jerome, CP, et al., "Effect of Treatment for 3 Months With Human Parathyroid Hormone 1-34 Peptide in Ovariectomized Cynomolgus Monkeys (*Macaca fascicularis* )," *Bone*, vol. 17, No. 4, Supplement, 415S-420S, (Oct. 1995).

Jerome, CP, et al., "Development of Osteopenia in Ovariectomized Cynomolgus Monkeys," *Bone*, vol. 17, No. 4, Supplment, pp. 403S-408S, (Oct. 1995).

Kalu, DN, et al., "Parathyroid Hormone and Experimental Osteosclerosis," *The Lancet*, Jun. 27, pp. 1363-1366, (1970).

Kim, HW, et al., "Effect of Recombinant Human (1-84) Parathyroid Hormone on Fracture Healing in Ovariectomized Rats", 43rd Annual Mtg., Orthopaedic Research Society, San Francisco, CA., (Feb. 9-13, 1997).

Lane, N, et al., "Parathyroid Hormone Treatment Can Reverse Corticosteroid-induced Osteoporosis," *J. Clin. Invest.*, vol. 102, No. 8, 1627-1633 (Oct. 1998).

Lilly Research Laboratories, "Teriparatide Injection NDA 21-318; Endocrinologic and Metabolic Drugs Advisory Committee Briefing Document," vol. 1, 1-128 (Jun. 15, 2001).

Lindsay, R, et al., "Randomised controlled study of effect of parathyroid hormone on vertebral-bone mass and fracture incidence among postmenopausal women on oestrogen with osteoporosis," *The Lancet*, vol. 350, 550-555 (1997).

Lindsay, R, et al., "Subcutaneous Administration of the Amino-Terminal Fragment of Human Parathyroid Hormone- (1-34): Kinetics and Biochemical Response in Estrogenized Osteoporotic Patients," *Journal of Clinical Endocrinology and Metabolism*, vol. 77, No. 6, 1535-1539 (1993).

Macgill, K, et al., "Vascular Effects of PTHrP (1-34) and PTH (1-34) in the Human Fetal-Placental circulation," *Placenta*, vol. 18, pp. 587-592 (1997).

Martindale, The Extra Pharmacoepia, The Pharmaceutical Press, London, 29th Ed. , p. 1338 (1998).

Masayuki, D., et al., "Bone mass-increasing effect of human PTH(1-34)," Grant-in-Aid Programs of the Ministry of Health, Comprehensive Study on Longevity Science, vol. 4, Geriatric Diseases, Particulars II, Osteoporosis, Study Report of 1997.

Neer, M, et al., "Treatment of Postmenopausal Osteoporosis with Daily Parathyroid Hormone Plus Calcitriol," *Osteoporosis International*, vol. 1 Supplement, S204-205 (1993).

Neer, RM, et al., "Effect of Parathyroid Hormone (1-34) on Fractures and Bone Mineral Density in Postmenopausal Women With Osteoporosis," *The New England Journal of Medicine*, vol. 334, No. 19 (May 10, 2001).

Neer, RM, et al., "The Use of Parathyroid Hormone Plus 1,25-dihyroxyvitamin D to Increase Trabecular Bone in Osteoporotic Men and Postmenopausal Women," *Osteoporosis*, vol. 2, 829-835 (1987).

Ohgitani, S, et al., "Calcium supplementation and parathyroid hormone," *Journal of Bone and Mineral Metabolism*, vol. 16, pp. 186-189, (1998).

Okimoto, N, et al., "Effects of weekly intermittent administration and withdrawal of human parathyroidhormone (1-34) on mechanical strength of cortical bone in ovariectomized rats, and historical mechanism of these effects," *Journal of Bone and Mineral Metabolism*, vol. 14, No. 4, pp. 177-181, (Jan. 1998).

Reeve, J, et al., "Anabolic Effect of Human Parathyroid Hormone Fragment on Trabecular Bone in Involutional Osteoporosis: A Multicentre Trial," *British Medical Journal*, vol. 280, 1340-1344 (1980).

Reeve, J, et al., "hPTH 1-34 Treatment of Osteoporosis with Added Hormone Replacement Therapy: Biochemical, Kinetic and Histological Responses," *Osteoporosis International*, vol. 1, 162-170 (1991).

Reeve, J, et al., "Human Parathyroid Peptide Treatment of Vertebral Osteoporosis," *Osteoporosis International*, vol. 1 Supplement, S199-203 (1993).

Reeve, J, et al., "Periodic courses of Human 1-34 Parathyroid Peptide Alternating With Calcitriol Paradoxically Reduce Bone Remodeling in spinal Osteoporosis," *European Journal of Clinical Investigation*, vol. 17, 421-428 (1987).

Reeve, J, et al., "The Therapeutic Use of Human Parathyroid Hormone Fragment (hPTH 1-34) in Osteoporosis: Optimizing the Anabolic Effect on Trabecular and Cortical Bone," *Monoclonal Antibodies and Developments in Immunoassay*, Proceedings of the 3rd International Conference on Radioimmunoassay 1981 held in Gardone Riviera, Italy, pp. 239-246, (May 6-9, 1981).

Reeve, J, et al., "Treatment of Osteoporosis with Human Parathyroid Peptide and Observations on Effect of Sodium Fluoride," *BMJ*, vol. 301, 134-318 (Aug. 11, 1990).

Reginster, JY, et al., "Parathyroid Hormone in the Treatment of Involutional Osteoporosis: Back to the Future," *Osteoporosis International*, vol. 7 Supplement 3, S163-S168 (1997).

Reid, IR, "The Roles of Clacium and Vitamin D in the Prevention of Osteoporosis," *Osteoporosis*, vol. 27, No. 2, pp. 389-398, (Jun. 1998).

Riggs, BL, et al., "Formation-Stimulating Regimens Other Than Sodium Fluoride," *The American Journal of Medicine*, vol. 95, Supplement 5A, 5A-62S-5A-68S (1993).

Riggs, BL, et al., "Involutional Osteoporosis,", *The New England Journal of Medicine*, vol. 314, No. 26, pp. 1676-1685, (Jun. 26, 1986).

Riggs, BL, et al., "Effect of Fluoride Treatment on the Fracture Rate in Postmenopausal Women with Osteoporosis," *The New England Journal of Medicine*, vol. 322, No. 12, pp. 802-809, (Mar. 22, 1990).

Rittmaster, RS, et al., "Treatment of Osteoporosis with Parathyroid Hormone Followed by Alendronate. Bone Market Results," *Bone*, vol. 23, (Suppl.), No. 5, S516-S517, Abstract F451 (1998).

Selye, H, et al., "On the Stimulation of New Bone-Formation with Parathyroid Extract and Irradiated Ergosterol," Department of Biochemistry, McGill University, pp. 547-552.

Slovik, DM, et al., "Restoration of Spinal Bone in Osteoporotic Men by Treatment With Human Parathyroid Hormone (1-34) and 1,25-Dihyroxyvitamin D," *Journal of Bone and Mineral Research*, vol. 1, No. 4, 377-381 (1986).

Slovik, DM, et al., "Renal 1,25-Dihydroxyvitamin D, Phosphaturic, And Cyclic-Amp Responses to Intravenous Synthetic Human Parathyroid Hormone (1-34) Administration in Normal Subjects," *Clinical Endocrinology*, vol. 20, pp. 369-375 (1984).

Slovik, DM, et al., "Short-term Effects of Synthetic Human Parathyroid Hormone-(1-34) Administration on Bone Mineral Metabolism in Osteoporotic Patients," *J Clin. Invest.*, vol. 68, pp. 1261-1271 (Nov. 1981).

Slovik, DM, et al., "Deficient Production of 1,25-Dihydroxyvitamin D in Elderly Osteoporotic Patients," *The New England Journal of Medicine*, vol. 305, No. 7, 372-374 (Aug. 13, 1981).

Smith, SY, et al., "Efficacy of Recombinant Human Parathyroid Hormone (1-84) (rhPTH, (1-84)) in Ovariectomized Rhesus Monkeys," *Journal of bone and Mineral Research*, vol. 23, No. 5, SA456 Abstract, S633 (1998).

Søgaard, CH, et al., "The Positive Effect of Parathyroid Hormone on Femoral Neck Bone Strength in Ovariectomized Rats Is More Pronounced That That of Estrogen or Bisphophonates," *Endocrinology*, vol. 134, No. 2, pp. 650-657, (1994).

Sone, T, et al., "A Small Dose of Human Parathyroid Hormone (1034) Increased Bone Mass in the Lumbar Vertebrae in Patients with Senile Osteoporosis," *Miner Electrolyte Metab.*, vol. 21, 232-235 (1995).

Whitfield, JF, et al., "Small Bone-Building Fragments of Parathyroid Hormone: New Therapeutic Agents for Osteoporosis," *TiPS*, vol. 16, 382-386 (Nov. 1995).

World Health Organization, Expert Committee on Biological Standardization, Geneva, Parathyroid Hormone, Bovine, For Bioassay, (Nov. 12-18, 1985).

Zanelli, JM, et al., The First International Reference Preparation of Human Parathyroid Hormone for Immunoassay: Characterization and Calibration by International Collaborative Study, *Journal of Clinical Endocrinology and Metabolism*, vol. 57, No. 3 (1983).

Zanelli, JM, et al., Biological Activities of Synthetic Human Parathyroid Hormone (PTH) 1-84 Relative to Natural Bovine 1-84 PTH in Two Different in Vivo Bioassay Systems, Endocrinology, vol. 117, No. 5, pp. 1962-1967 (Nov. 1985).

OP Written Decision dated Feb. 17, 2006 for 99 942 350.2—2107, 1059933.

Lilly Grounds of Appeal, Jul. 23, 2006, European Patent No. 1059933, Eli Lilly and Company Opposed by Daiichi Suntory Pharma Co., Ltd., et al.

Opposition Grounds of Appeal, Appeal Proceedings Number: T 0610/06-3304, Opposition to European patent No. 1059933 B1 (Application No. 99942350.2) dated May 7, 2006.

Lilly's Response to Grounds of Appeal, European Patent No. 1059933 dated Nov. 14, 2006.

Opposition Response to Grounds of Appeal, Appeal Proceedings Number: T 0610/06-3304, Opposition to European patent No. 1059933 B1 (Application No. 99942350.2) dated Nov. 15, 2006.

* cited by examiner

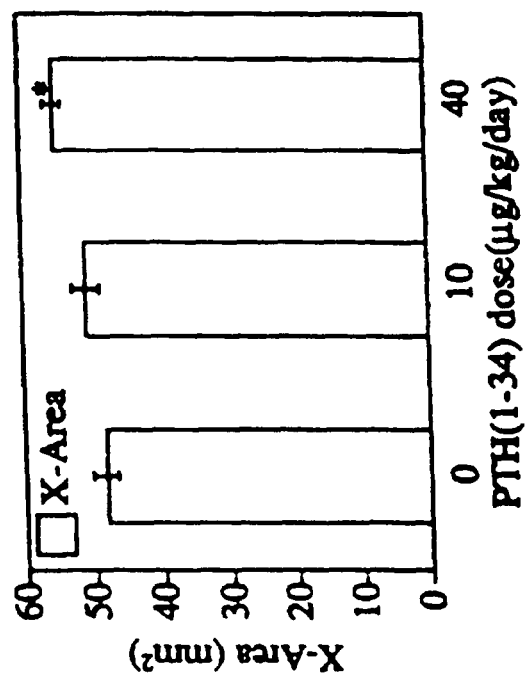
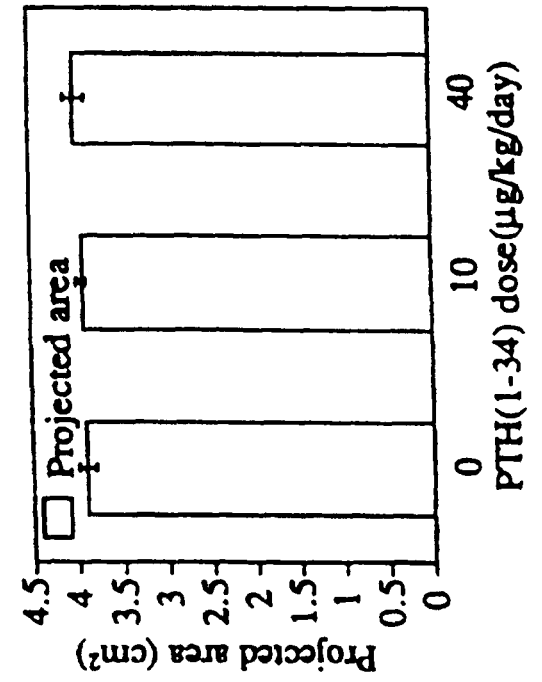
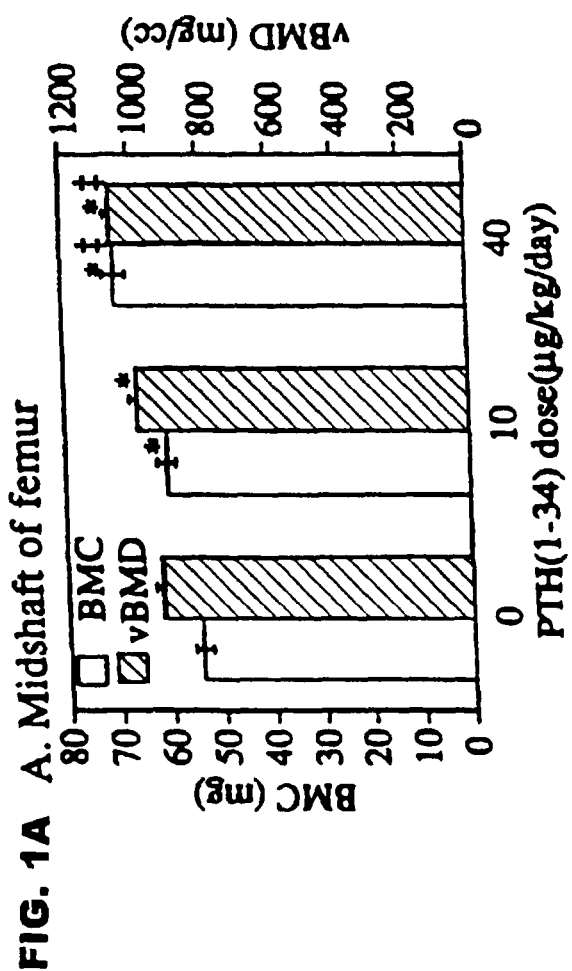
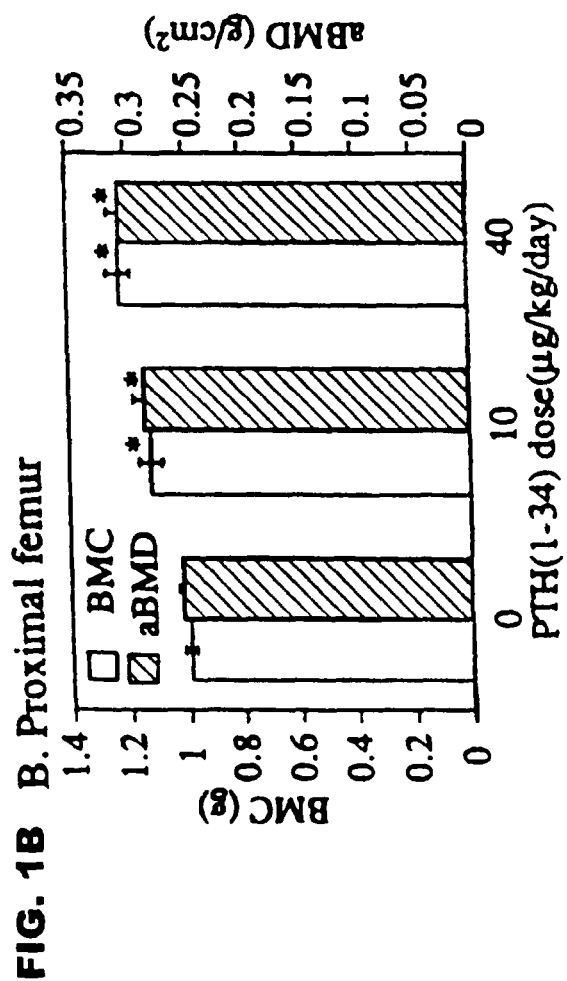
FIG. 1A A. Midshaft of femur
FIG. 1B B. Proximal femur

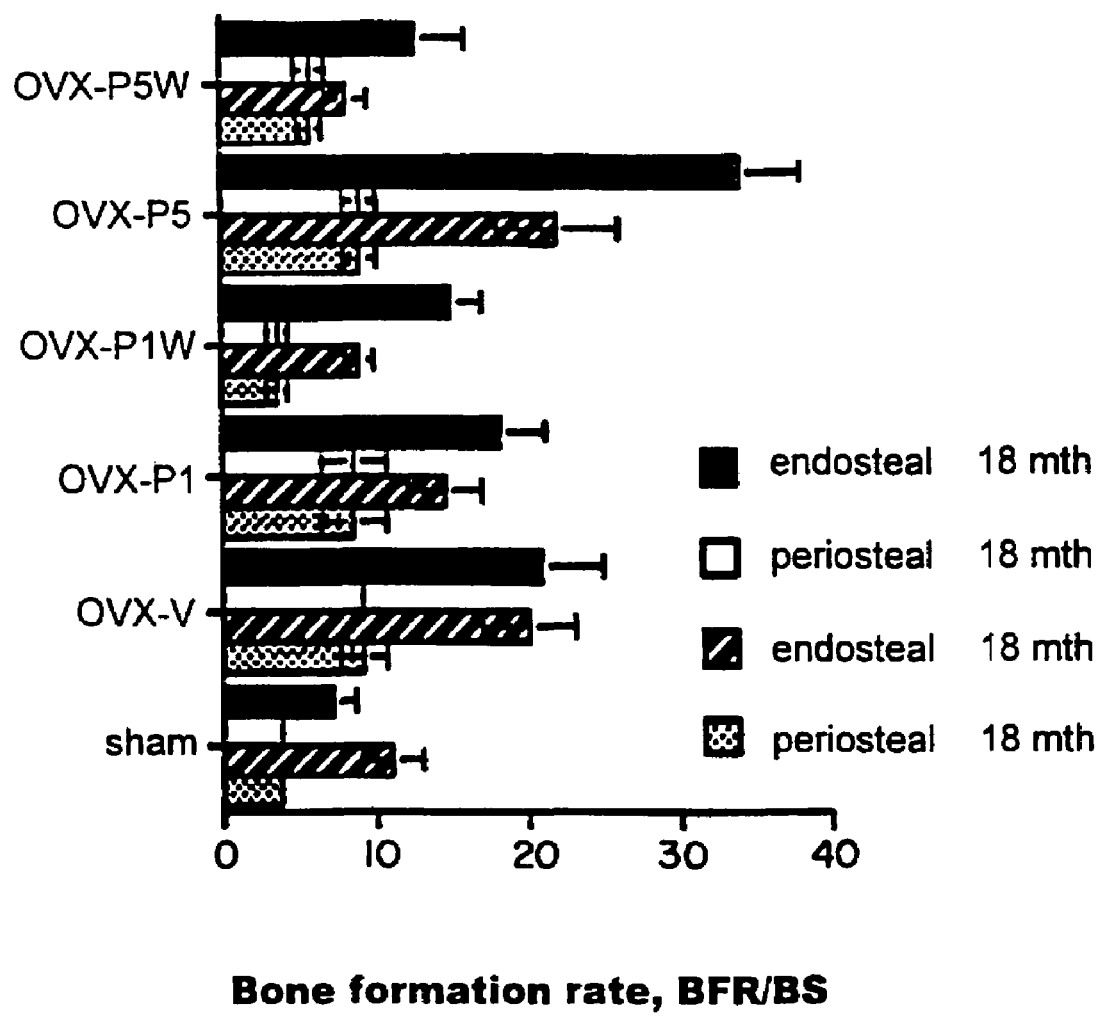

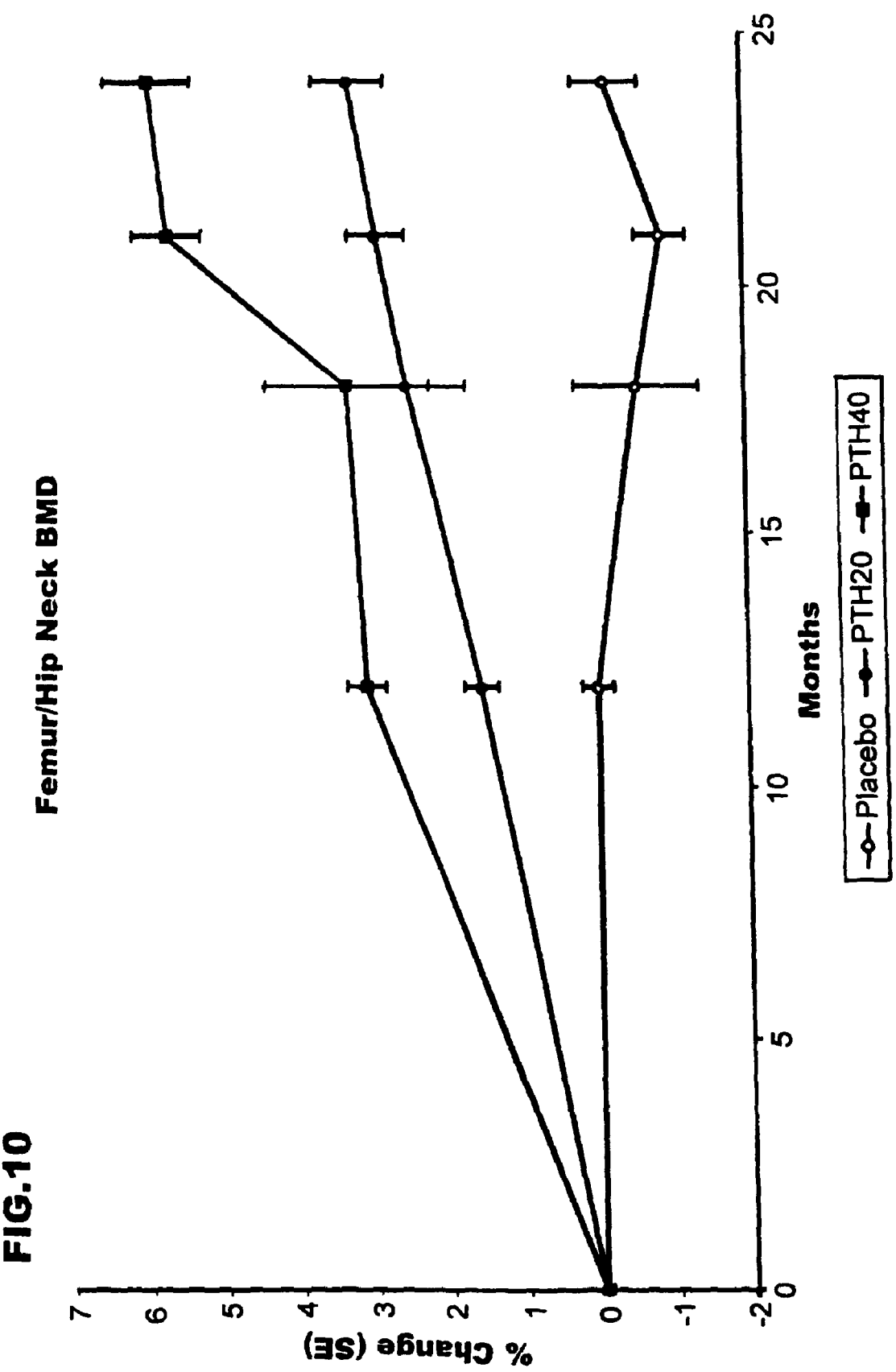

METHOD OF REDUCING THE RISK OF BONE FRACTURE

This application is a continuation of Ser. No. 11/098,909 filed Apr. 5, 2005, now abandoned which is a continuation of Ser. No. 10/443,693 filed May 22, 2003, now abandoned, which is a continuation of Ser. No. 09/647,278 filed Sep. 26, 2000 that issued as U.S. Pat. No. 6,977,077 and which is a §371 filing of PCT/US 99/18961 filed Aug. 19, 1999, which claims the benefit of Provisional Application No. 60/097,151, filed Aug. 19, 1998, and Provisional Application No. 60/099,746, filed Sep. 10, 1998,

TECHNICAL FIELD

This invention relates to methods for increasing the toughness and/or stiffness of bone and/or reducing the likelihood and/or severity of bone fracture by administering a parathyroid hormone. More particularly, the invention relates a method for increasing toughness or stiffness of bone at a site of a potential or actual trauma, such as the hip or spine of a person at risk of or suffering from osteoporosis. More particularly, the invention relates to a method of reducing the incidence of vertebral fracture, reducing the incidence of multiple vertebral fractures, reducing the severity of vertebral fracture, and/or reducing the incidence of non-vertebral fracture.

BACKGROUND OF THE INVENTION

Existing agents such as estrogen, bisphosphonates, fluoride, or calcitonin can prevent bone loss and induce a 3-5% increase of bone mass by refilling the remodeling space, but net bone formation is not significantly stimulated. The retention of bone by inhibition of bone turnover may not be sufficient protection against fracture risk for patients who already have significant bone loss. Anabolic agents that increase bone strength by stimulating bone formation preferentially may provide better protection against fracture in patients with established osteoporosis.

Parathyroid hormone (PTH) is a secreted, 84 amino acid product of the mammalian parathyroid gland that controls serum calcium levels through its action on various tissues, including bone. The N-terminal 34 amino acids of bovine and human PTH (PTH(1-34)) is deemed biologically equivalent to the full length hormone. Other amino terminal fragments of PTH (including 1-31 and 1-38 for example), or PTHrP (PTH-related peptide/protein) or analogues of either or both, that activate the PTH/PTHrP receptor (PTHI receptor) have shown similar biologic effects on bone mass, although the magnitude of such effects may vary.

Studies in humans with various forms of PTH have demonstrated an anabolic effect on bone, and have prompted significant interest in its use for the treatment of osteoporosis and related bone disorders. The significant anabolic effects of PTH on bone, including stimulation of bone formation which results in a net gain in bone mass and/or strength, have been demonstrated in many animal models and in humans.

It is commonly believed that PTH administration in humans and in relevant animal models has a negative effect on cortical bone. In fact, naturally occurring increases in endogenous PTH, which occur in the disorder hyperparathyroidism, result in thinning of cortical bone accompanied by an increase in connectivity and mass of trabecular bone. Past studies suggest that when Haversian cortical bone (found in humans and higher mammals) remodels under the influence of PTH, there will be a re-distribution of bone such that cortical bone mass and strength decrease, while trabecular bone increases in mass and strength. For example, in published clinical studies of administering PTH, cortical bone mass decreased after treatment with exogenous PTH and these findings have raised concern that the treatment of PTH will lead to reduced cortical bone mass and strength. One concern raised by such studies is that there would be a loss of total skeletal bone mass due to the loss of cortical bone. This is of high clinical relevance as, in osteoporosis, the greater loss of trabecular bone compared to loss of cortical bone, means that mechanical loading is predominantly borne by the remaining cortical bone. Continued loss of cortical bone would increase the fracture risk. Therefore, it is important that a therapeutic agent for osteoporosis maintain or increase a subjects residual cortical bone.

The effects of PTH on cortical bone have been investigated in nonhuman animals with Haversian remodeling, such as dogs, ferrets, sheep and monkeys, but sample sizes are typically too small for reliable statistical analysis. The impact of the changes induced by PTH treatment on mechanical properties of cortical bone in such animals remains unknown. Published studies of rodents have shown increased cortical bone mass during administration of PTH but a loss of this benefit after withdrawal of PTH. However, rodent cortical bone has a distinctly different structure from Haversian cortical bone, and remodels by surface appositional formation and resorption, rather than by intracortical remodeling of osteons. Furthermore, technological limitations in biomechanical testing on the relatively short bones of rodents give rise to artifacts of measurement when an agent, such as a PTH, alters bone geometry to thicken the bone. Such artifacts make extrapolation of rat cortical bone responses to those of humans or other animals with osteonal remodeling unreliable. Therefore, the existing data for animals, like humans, undergoing Haversian remodeling indicates that PTH may have an adverse impact on cortical bone, causing net loss of bone mass through depletion of cortical bone.

As a consequence, it has been a popular belief regarding the action of PTH that patients require concurrent or subsequent treatment with an antiresorptive to minimize loss of bone induced by PTH. In fact, this model has been the basis for several clinical studies in women. For example, three clinical studies have used PTH in post-menopausal women on concurrent therapy with calcitonin or estrogen, or in premenopausal women taking GnRH agonist, Synarel, for endometriosis. The opposing effects of estrogen and PTH on cortical bone turnover make it particularly difficult to observe effects of just PTH during combination therapy with these two agents.

There remains a need for a method for employing a PTH to increase strength and stiffness of bone in humans and other animals exhibiting Haversian remodeling, and for reducing the incidence of fracture of bones in these animals. Furthermore, there remains a need for a method for increasing the quality and amount of cortical bone.

SUMMARY OF THE INVENTION

The present invention includes a method for increasing the toughness and/or stiffness of bone, preferably cortical bone, and/or reducing the incidence and/or severity of fracture by administering a parathyroid hormone. More particularly, the invention relates to a method for increasing toughness or stiffness of bone at a site of a potential or actual trauma. Increasing toughness and/or stiffness of bone can be manifested in numerous ways known to those of skill in the art, such as increasing bone mineral density, increasing bone mineral content, increasing work to failure, and the like. In one embodiment, the method of the invention reduces the incidence or severity of vertebral and/or non-vertebral fractures. The method of the invention can be used to decrease the risk of such fractures or for treating such fractures. In particular, the method of the invention can reduce the incidence of vertebral and/or non-vertebral fracture, reduce the severity of vertebral fracture, reduce the incidence of multiple vertebral fracture, improve bone quality, and the like.

The method can increase toughness or stiffness at a site of a potential trauma, such as a hip or spine of a person with osteoporosis, or at another site having abnormally low bone mass or poor bone structure. The method can also increase bone toughness or stiffness at a site of an actual trauma, such as a fracture, for example, in a hip or vertebra. A preferred subject for the method of the invention is a woman or man at risk for or having osteoporosis, preferably a postmenopausal woman, and is independent of concurrent hormone replacement therapy (HRT), estrogen or equivalent therapy, or antiresorptive therapy. In one embodiment, the patient also receives supplements of calcium and/or vitamin D.

A parathyroid hormone, such as the N-terminal amino acids 1-34 of recombinant human parathyroid hormone, can be administered either cyclically or intermittently. Preferably, cyclic administration includes administering PTH for 2 or more remodeling cycles and withdrawing PTH for one or more remodeling cycles. Further, according to the method of the invention, the increases in toughness and/or stiffness of a bone can persist for several remodeling cycles, or up to several years, after the last administration of a parathyroid hormone.

BRIEF DESCRIPTION OF THE DRAWINGS

FIGS. 1A and 1B show that BMD (bone mineral density) and BMC (bone mineral content) in the femoral midshaft (cortical bone) (A) and in the proximal femur (cancellous bone+cortical bone) (B) were significantly greater in PTH-treated animals than controls at both doses.

FIG. 7 illustrates activation of bone formation rates on endosteal and periosteal surfaces of the midshaft humerus.

FIG. 10 illustrates increases in femur and hip neck BMD through 24 months of treatment of patients with either 20 µg/kg/day PTH or 40 µg/kg/day PTH, compared to placebo treated controls.

DETAILED DESCRIPTION

Figure 2A:
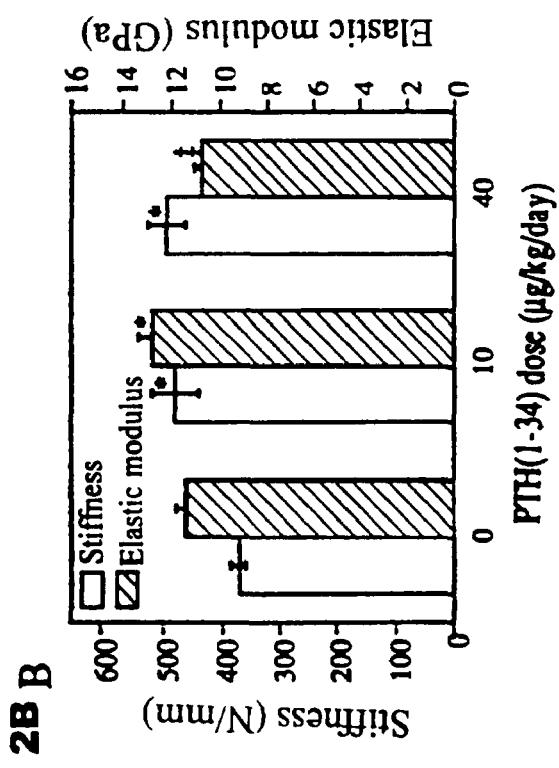
FIGS. 2A through 2D show the effects of PTH on mechanical strength and cross sectional moment of inertia (CSMI) in the cortical bone of the femoral midshaft.
Figure 2B:
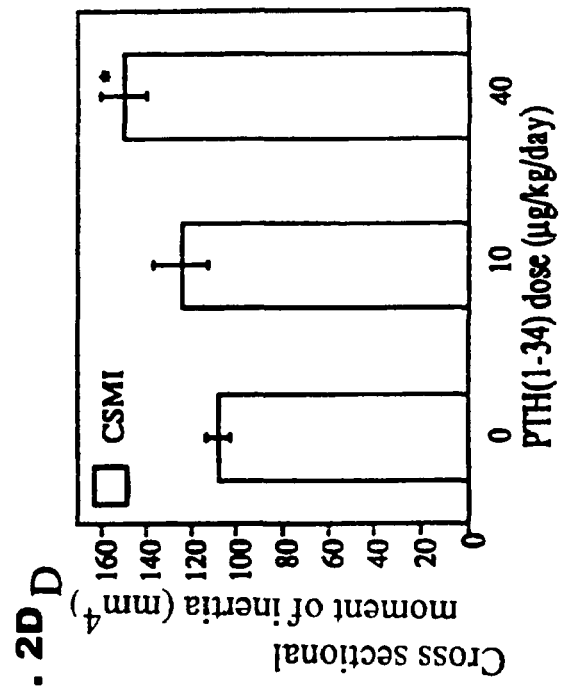
Figure 2C:
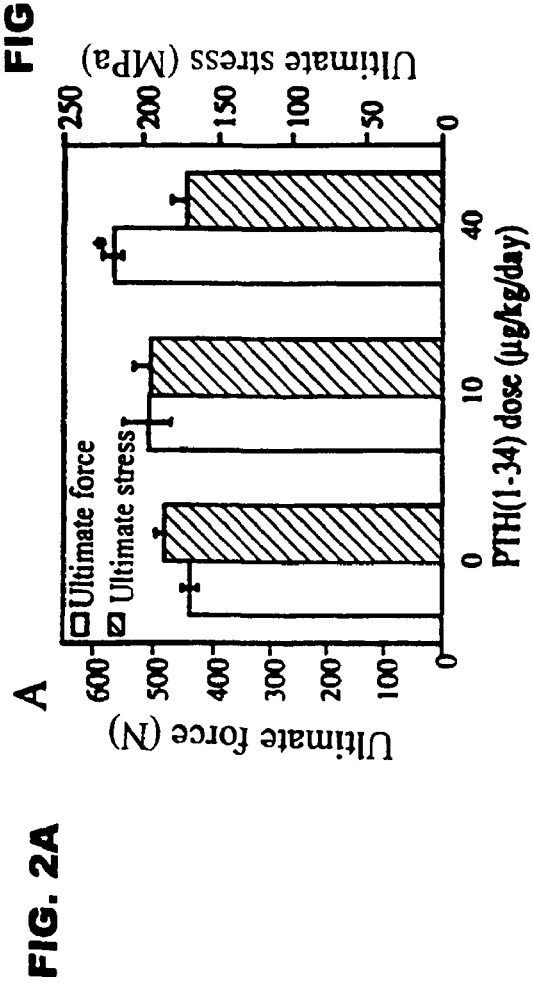
Figure 2D:
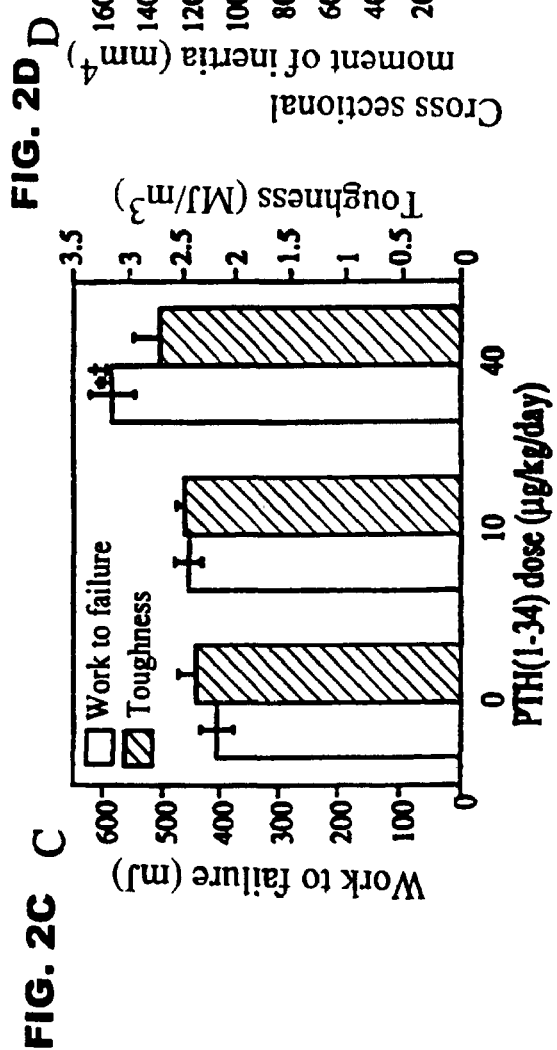

The invention relates to a method for increasing bone toughness and/or stiffness, and/or reducing incidence of fracture in a subject by administering a parathyroid hormone. The method can be employed to increase stiffness and/or toughness at a site of a potential trauma or at a site of an actual trauma. Trauma generally includes fracture, surgical trauma, joint replacement, orthopedic procedures, and the like. Increasing bone toughness and/or stiffness generally includes increasing mineral density of cortical bone, increasing strength of bone, increasing resistance to loading, and the like. Reducing incidence of fracture generally includes reducing the likelihood or actual incidence of fracture for a subject compared to an untreated control population.

As used herein, ultimate force refers to maximum force that a bone specimen sustains; stiffness refers to the slope of the linear portion of a load-deformation curve; and work to failure refers to the area under the load-deformation curve before failure. Each of these can be measured and calculated by methods standard in the bone study art. These parameters are structural properties that depend on intrinsic material properties and geometry, and can be determined as described in Turner CH, Burr DB 1993 "Basic biomechanical measurements of bone: a tutorial." *Bone* 14:595-608, which is incorporated herein by reference. Ultimate force, stiffness, and work to failure can be normalized to obtain intrinsic material properties such as ultimate stress, elastic modulus, and toughness, which are independent of size and shape. As used herein, ultimate stress refers to maximum stress that a specimen can sustain; elastic modulus refers to material intrinsic stiffness; and toughness refers to resistance to fracture per unit volume. Each of these can be determined by methods known in the art. Id. Femoral bone strength, as referred to herein, can be measured at the femur neck, or at the midshaft typically using three-point or four-point bending at the latter site.

Bone Trauma

The method of the invention is of benefit to a subject that may suffer or have suffered trauma to one or more bones. The method can benefit mammalian subjects, such as humans, horses, dogs, and cats, in particular, humans. Bone trauma can be a problem for racing horses and dogs, and also for household pets. A human can suffer any of a variety of bone traumas due, for example, to accident, medical intervention, disease, or disorder. In the young, bone trauma is likely due to fracture, medical intervention to repair a fracture, or the repair of joints or connective tissue damaged, for example, through athletics. Other types of bone trauma, such as those from osteoporosis, degenerative bone disease (such as arthritis or osteoarthritis), hip replacement, or secondary conditions associated with therapy for other systemic conditions (e.g., glucocorticoid osteoporosis, burns or organ transplantation) are found most often in older people.

Preferred subjects include a human, preferably a woman, at risk for or suffering from osteoporosis. Risk factors for osteoporosis are known in the art and include hypogonadal conditions in men and women, irrespective of age, conditions, diseases or drugs that induce hypogonadism, nutritional factors associated with osteoporosis (low calcium or vitamin D being the most common), smoking, alcohol, drugs associated with bone loss (such as glucocorticoids, thyroxine, heparin, lithium, anticonvulsants etc.), loss of eyesight that predisposes to falls, space travel, immobilization, chronic hospitalization or bed rest, and other systemic diseases that have been linked to increased risk of osteoporosis. Indications of the presence of osteoporosis are known in the art and include radiological evidence of at least one vertebral compression fracture, low bone mass (typically at least 1 standard deviation below mean young normal values), and/or atraumatic fractures.

Osteoporosis can lead, for example, to vertebral and/or non-vertebral fractures. Examples of non-vertebral fractures include a hip fracture, a fracture of a distal forearm, a fracture of a proximal humerus, a fracture of a wrist, a fracture of a radius, a fracture of an ankle, a fracture of an humerus, a fracture of a rib, a fracture of a foot, a fracture of a pelvis, or a combination of these. The method of the invention can be used to decrease the risk of such fractures or for treating such fractures. The risk of fracture is diminished and the healing of a fracture is aided by increasing the strength and/or stiffness of bone, for example, in the hip, the spine or both. A typical woman at risk for osteoporosis is a postmenopausal woman or a premenopausal, hypogonadal woman. A preferred subject is a postmenopausal woman, and is independent of concurrent hormone replacement therapy (HRT), estrogen or equivalent therapy, or antiresorptive therapy. The method of invention can benefit a subject at any stage of osteoporosis, but especially in the early and advanced stages.

The present invention provides a method, in particular, effective to prevent or reduce the incidence of fractures in a subject with or at risk of progressing to osteoporosis. For example, the present invention can reduce the incidence of vertebral and/or non-vertebral fracture, reduce the severity of vertebral fracture, reduce the incidence of multiple vertebral fracture, improve bone quality, and the like. In another embodiment, the method of the present invention can benefit patients with low bone mass or prior fracture who are at risk for future multiple skeletal fractures, such as patients in which spinal osteoporosis may be progressing rapidly.

Other subjects can also be at risk of or suffer bone trauma and can benefit from the method of the invention. For example, a wide variety of subjects at risk of one or more of the fractures identified above, can anticipate surgery resulting in bone trauma, or may undergo an orthopedic procedure that manipulates a bone at a skeletal site of abnormally low bone mass or poor bone structure, or deficient in mineral. For example, recovery of function after a surgery such as a joint replacement (e.g. knee or hip) or spine bracing, or other procedures that immobilize a bone or skeleton can improve due to the method of the invention. The method of the invention can also aid recovery from orthopedic procedures that manipulate a bone at a site of abnormally low bone mass or poor bone structure, which procedures include surgical division of bone, including osteotomies, joint replacement where loss of bone structure requires restructuring with acetabulum shelf creation and prevention of prosthesis drift, for example. Other suitable subjects for practice of the present invention include those suffering from hypoparathyroidism or kyphosis, who can undergo trauma related to, or caused by, hypoparathyroidism or progression of kyphosis.

Bone Toughness and Stiffness

The method of the invention reduces the risk of trauma or aids recovery from trauma by increasing bone toughness, stiffness or both. Generally toughness or stiffness of bone results from mass and strength of cortical, trabecular, and cancellous bone. The method of the invention can provide levels of bone toughness, stiffness, mass, and/or strength within or above the range of the normal population. Preferably the invention provides increased levels relative to the levels resulting from trauma or giving rise to risk of trauma. Increasing toughness, stiffness, or both decreases risk or probability of fracture compared to an untreated control population.

Certain characteristics of bone when increased provide increased bone toughness and/or stiffness. Such characteristics include bone mineral density (BMD), bone mineral content (BMC), activation frequency or bone formation rate, trabecular number, trabecular thickness, trabecular and other connectivity, periosteal and endocortical bone formation, cortical porosity, cross sectional bone area and bone mass, resistance to loading, and/or work to failure. An increase in one or more of these characteristics is a preferred outcome of the method of the invention.

Certain characteristics of bone, such as marrow space and elastic modulus when decreased provide increased toughness and/or stiffness of bone. Younger (tougher and stiffer) bone has crystallites that are generally smaller than crystallites of older bone. Thus, generally reducing the size of bone crystallites increases toughness and stiffness of bone, and can reduce incidence of fracture. In addition, maturing the crystallites of a bone can provide additional desirable characteristics to the bone, including increased toughness and stiffness of bone and/or can reduced incidence of fracture. A decrease in one or more of these characteristics can be a preferred outcome of the method of the invention.

The method of the invention is effective for increasing the toughness and/or stiffness of any of several bones. For example, the present method can increase the toughness and/or stiffness of bones including a hip bone, such as an ilium, a leg bone, such as a femur, a bone from the spine, such as a vertebra, or a bone from an arm, such as a distal forearm bone or a proximal humerus. This increase in toughness and/or stiffness can be found throughout the bone, or localized to certain portions of the bone. For example, toughness and/or stiffness of a femur can be increased by increasing the toughness and/or stiffness of a femur neck or a femur trochantera. Toughness and/or stiffness of a hip can be increased by increasing the toughness and/or stiffness of an iliac crest or iliac spine. Toughness and/or stiffness of a vertebra can be increased by increasing the toughness and/or stiffness of a pedicle, lamina, or body. Advantageously, the effect is on vertebra in certain portions of the spine, such as cervical, thoracic, lumbar, sacral, and/or coccygeal vertebrae. Preferably the effect is on one or more mid-thoracic and/or upper lumbar vertebrae.

The increase in toughness and/or stiffness can be found in each of the types of bone, or predominantly in one type of the bone. Types of bone include spongy (cancellous, trabecular, or lamellar) bone and compact (cortical or dense) bone and the fracture callus. The method of the invention preferably increases toughness and/or stiffness through its effects on cancellous and cortical bone, or on cortical bone alone. Trabecular bone, bone to which connective tissue is attached can also be toughened and/or stiffened by the present method. For example, it is advantageous to provide additional toughness at a site of attachment for a ligament, a tendon, and/or a muscle.

In another aspect of the invention, increasing toughness or stiffness can reduce incidence of fracture. In this aspect, increasing toughness or stiffness can include reducing incidence of vertebral fracture, reducing incidence of severe fracture, reducing incidence of moderate fracture, reducing incidence of non-vertebral fracture, reducing incidence of multiple fracture, or a combination thereof.

Parathyroid Hormone

As active ingredient, the composition or solution may incorporate the full length, 84 amino acid form of parathyroid hormone, particularly the human form, hPTH (1-84), obtained either recombinantly, by peptide synthesis or by extraction from human fluid. See, for example, U.S. Pat. No. 5,208,041, incorporated herein by reference. The amino acid sequence for hPTH (1-84) is reported by Kimura et al. in Biochem. Biophys. Res. Comm., 114(2):493.

The composition or solution may also incorporate as active ingredient fragments or variants of fragments of human PTH or of rat, porcine or bovine PTH that have human PTH activity as determined in the ovariectomized rat model of osteoporosis reported by Kimmel et al., Endocrinology, 1993, 32(4):1577.

The parathyroid hormone fragments desirably incorporate at least the first 28 N-terminal residues, such as PTH(1-28), PTH(1-31), PTH(1-34), PTH(1-37), PTH(1-38) and PTH(1-41). Alternatives in the form of PTH variants incorporate from 1 to 5 amino acid substitutions that improve PTH stability and half-life, such as the replacement of methionine residues at positions 8 and/or 18 with leucine or other hydrophobic amino acid that improves PTH stability against oxidation and the replacement of amino acids in the 25-27 region with trypsin-insensitive amino acids such as histidine or other amino acid that improves PTH stability against protease. Other suitable forms of PTH include PTHrP, PTHrP(1-34), PTHrP(1-36) and analogs of PTH or PTHrP that activate the PTH1 receptor. These forms of PTH are embraced by the term "parathyroid hormone" as used generically herein. The hormones may be obtained by known recombinant or synthetic methods, such as described in U.S. Pat. Nos. 4,086,196 and 5,556,940, incorporated herein by reference.

The preferred hormone is human PTH(1-34), also known as teriparatide. Stabilized solutions of human PTH(1-34), such as recombinant human PTH(1-34) (rhPTH(1-34), that can be employed in the present method are described in U.S. patent application Ser. No. 60/069,075, incorporated herein by reference. Crystalline forms of human PTH(1-34) that can be employed in the present method are described in U.S. patent application Ser. No. 60/069,875, incorporated herein by reference.

Administering Parathyroid Hormone

A parathyroid hormone can typically be administered parenterally, preferably by subcutaneous injection, by methods and in formulations well known in the art. Stabilized formulations of human PTH(1-34) that can advantageously be employed in the present method are described in U.S. patent application Ser. No.60/069,075, incorporated heroin by reference. This patent application also describes numerous other formulations for storage and administration of parathyroid hormone. A stabilized solution of a parathyroid hormone can include a stabilizing agent, a buffering agent, a preservative, and the like.

The stabilizing agent incorporated into the solution or composition includes a polyol which includes a saccharide, preferably a monosaccharide or disaccharide, e.g., glucose, trehalose, raffinose, or sucrose; a sugar alcohol such as, for example, mannitol, sorbitol or inositol, and a polyhydric alcohol such as glycerine or propylene glycol or mixtures thereof. A preferred polyol is mannitol or propylene glycol. The concentration of polyol may range from about 1 to about 20 wt-%, preferably about 3 to 10 wt-% of the total solution.

The buffering agent employed in the solution or composition of the present invention may be any acid or salt combination which is pharmaceutically acceptable and capable of maintaining the aqueous solution at a pH range of 3 to 7, preferably 3-6. Useful buffering systems are, for example, acetate, tartrate or citrate sources. Preferred buffer systems are acetate or tartrate sources, most preferred is an acetate source. The concentration of buffer may be in the range of about 2 mM to about 500 mM, preferably about 2 mM to 100 mM.

The stabilized solution or composition of the present invention may also include a parenterally acceptable preservative. Such preservatives include, for example, cresols, benzyl alcohol, phenol, benzalkonium chloride, benzethonium chloride, chlorobutanol, phenylethyl alcohol, methyl paraben, propyl paraben, thimerosal and phenylmercuric nitrate and acetate. A preferred preservative is m-cresol or benzyl alcohol; most preferred is m-cresol. The amount of preservative employed may range from about 0.1 to about 2 wt-%, preferably about 0.3 to about 1.0 wt-% of the total solution.

Thus, the stabilized teriparatide solution can contain mannitol, acetate and m-cresol with a predicted shelf-life of over 15 months at 5° C.

The parathyroid hormone compositions can, if desired, be provided in a powder form containing not more than 2% water by weight, that results from the freeze-drying of a sterile, aqueous hormone solution prepared by mixing the selected parathyroid hormone, a buffering agent and a stabilizing agent as above described. Especially useful as a buffering agent when preparing lyophilized powders is a tartrate source. Particularly useful stabilizing agents include glycine, sucrose, trehalose and raffinose.

In addition, parathyroid hormone can be formulated with typical buffers and excipients employed in the art to stabilize and solubilize proteins for parenteral administration. Art recognized pharmaceutical carriers and their formulations are described in Martin, "Remington's Pharmaceutical Sciences," 15th Ed.; Mack Publishing Co., Easton (1975). A parathyroid hormone can also be delivered via the lungs, mouth, nose, by suppository, or by oral formulations.

The parathyroid hormone is formulated for administering a dose effective for increasing toughness and/or stiffness of one or more of a subject's bones and/or for reducing the likelihood and/or severity of bone fracture. Preferably, an effective dose provides an improvement in cortical bone structure, mass, and/or strength. Preferably, an effective dose reduces the incidence of vertebral fracture, reduces the incidence of multiple vertebral fractures, reduces the severity of vertebral fracture, and/or reduces the incidence of non-vertebral fracture. Preferably, a subject receiving parathyroid hormone also receives effective doses of calcium and vitamin D, which can enhance the effects of the hormone. An effective dose of parathyroid hormone is typically greater than about 5 μg/kg/day although, particularly in humans, it can be as large at about 10 to about 40 μg/kg/day, or larger as is effective to achieve increased toughness or stiffness, particularly in cortical bone, or to reduce the incidence of fracture. A subject suffering from hypoparathyroidism can require additional or higher doses of a parathyroid hormone; such a subject also requires replacement therapy with the hormone. Doses required for replacement therapy in hypoparathyroidism are known in the art. In certain instances, relevant effects of PTH can be observed at doses less than about 5 μg/kg/day, or even less than about 1 μg/kg/day.

The hormone can be administered regularly (e.g., once or more each day or week), intermittently (e.g., irregularly during a day or week), or cyclically (e.g., regularly for a period of days or weeks followed by a period without administration). Preferably PTH is administered once daily for 1-7 days for a period ranging from 3 months for up to 3 years in osteoporotic patients. Preferably, cyclic administration includes administering a parathyroid hormone for at least 2 remodeling cycles and withdrawing parathyroid hormone for at least 1 remodeling cycle. Another preferred regime of cyclic administration includes administering the parathyroid hormone for at least about 12 to about 24 months and withdrawing parathyroid hormone for at least 6 months. Typically, the benefits of administration of a parathyroid hormone persist after a period of administration. The benefits of several months of administration can persist for as much as a year or two, or more, without additional administration.

Uses of Formulations of a Parathryoid Hormone

The present invention also encompasses a kit including the present pharmaceutical compositions and to be used with the methods of the present invention. The kit can contain a vial which contains a formulation of the present invention and suitable carriers, either dried or in liquid form. The kit further includes instructions in the form of a label on the vial and/or in the form of an insert included in a box in which the vial is packaged, for the use and administration of the compounds. The instructions can also be printed on the box in which the vial is packaged. The instructions contain information such as sufficient dosage and administration information so as to allow a worker in the field to administer the drug. It is anticipated that a worker in the field encompasses any doctor, nurse, or technician who might administer the drug.

The present invention also relates to a pharmaceutical composition including a formulation of one or more parathyroid hormones, such as human PTH(1-84) or human PTH(1-34), and that is suitable for parenteral administration. According to the invention, a formulation of one or more parathyroid hormones, such as human PTH(1-84) or human PTH(1-34), can be used for manufacturing a composition or medicament suitable for administration by parenteral administration. The invention also relates to methods for manufacturing compositions including a formulation of one or more parathyroid hormones, such as human PTH(1-84) or human PTH(1-34), in a form that is suitable for parenteral administration. For example, a liquid or solid formulation can be manufactured in several ways, using conventional techniques. A liquid formulation can be manufactured by dissolving the one or parathyroid hormones, such as human PTH(1-84) or human PTH(1-34), in a suitable solvent, such as water, at an appropriate pH, including buffers or other excipients, for example to form one of the stabilized solutions described hereinabove.

The examples which follow are illustrative of the invention and are not intended to be limiting.

EXAMPLES

Example 1

Increased Bone Strength and Density Upon Administration of rhPTH(1-34) to Rabbits Experimental Procedures Female intact New Zealand white rabbits (HRP Inc. Denver, Pa.), one of the smallest animals that form osteons by intracortical remodeling, approximately 9 months old and weighing 3.25-3.75 kg, were sorted by mean group body weight into 3 groups of 6 animals each. Two experimental groups received biosynthetic PTH(1-34) at doses of 10 or 40 μg/ml/kg/day. The control group was given 1.0 ml/kg/day of acidified 0.9M saline containing 2% heat-inactivated rabbit sera. PTH(1-34) or vehicle were injected by once daily subcutaneous injections on 5 days a week for 140 days. Rabbits were fed rabbit lab chow containing 0.5% Ca and 0.41%P, and given water ad libitum.

The selection of doses was based on a series of preliminary studies showing that (1) after a single injection of PTH(1-34) at 100 pg/kg, serum calcium increased and failed to return to baseline by 24 hours, whereas after a single dose of 50 μg/kg, serum calcium returned to baseline within 24 hours, (2) repeated injections of 20 μg/kg PTH(1-34) resulted in transient rise in serum calcium with return to baseline values in 6-24 hours, and (3) PTH(1-34) at $\leq 5$ μg/kg did not alter histomorphometry of bone surfaces.

A set of double alizarin labels (Sigma, St. Louis) was given i.m. at 20 mg/kg on days 55 and 63, and a set of double calcein labels (Sigma, St. Louis) was given s.c. at 5 mg/kg on days 15 and 7, prior to sacrifice. Rabbits were anesthetized by $CO_2$ in a random order sequence, approximately 3-6 hours after the last injection, to obtain blood by cardiac puncture and then killed with sodium pentobarbital (100 mg/kg), injected i.p. The right humerus, both femora, lumbar vertebrae (L3-L5) and the right tibia were removed.

Blood Chemistry

Serum calcium, phosphate, alkaline phosphatase, creatinine and urea nitrogen were measured by computerized multichannel serum analysis.

Histomorphometry

Histomorphometric measurements were done on cortical bone of tibial midshaft and on cancellous bone of L3. After sacrifice, these bones were removed from each animal and fixed in 10% neutral buffered formalin for 24 hours. The tissues were dehydrated in a graded series of alcohols (70-100%, 2 changes per grade, each for 4 hours under vacuum). The specimens were then placed in xylene, and infiltrated with methylmethacrylate under vacuum at 20 psi on 2 hours/step and 24 hours infiltration schedule in a Shandon Hypercenter automatic processor (Shandon Lipshaw, Pittsburgh, Pa.). The specimens were embedded in 2% DDK-plast with 0.2% initiator (Delaware Diamond Knives, Wilmington, Del.). Cross-sections of tibia were cut at 80 μm using a diamond wire saw (Delaware Diamond Knives, Inc., Del.) and stained with Goldner's trichrome. Unstained cross sections approximately 80 μm thick were processed for dynamic histomorphometry of fluorochrome labels. Sagittal sections of L3 were cut on Reichert-Jung 2050 microtome (Magee Scientific Inc., Dexter, Mich.) at 5 μm and stained with McNeal's tetrachrome, or left unstained for dynamic histomorphometry.

Histomorphometry was done at 150× magnification, using a Nikon fluorescence microscope (Optiphot, Nikon, Tokyo, Japan) and a semi-automatic digitizing system (Bioquant IV, R&M Biometrics, Nashville, Tenn.). Bone formation and resorption in the periosteal, endocortical and intracortical envelopes were measured across the entire cross-sectional area of the mid-diaphyseal sections of the tibia. Measurements on cancellous bone were made within a 6 $mm^2$-area in the center of the lumbar vertebra, 0.5 mm from the margin of the surrounding cortical shell. The nomenclature was in accordance with the ASBMR Committee on histomorphometric nomenclature (Parfitt A M, Drezner M K, Florieux F H, Kanis J A, Malluche H, Meunier P J, Ott S M, Recker R R 1987 "Bone histomorphometry: standardization of nomenclature, symbols, and units. Report of the ASBMR Histomorphometry Nomenclature Committee". *J. Bone Miner. Res.* 2:595-610.) Dynamic parameters were measured based on the calcein label.

Bone Mass Measurements

The mid-shaft of femora and the fourth lumbar vertebra in 50% ethanol/saline were scanned in cross-section by quantitated computer tomography (QCT or pQCT) employing a 960A pQCT and analyzed using Dichte software version 5.1 (Norland/Stratec, Ft. Atkinson, Wis.). Whole tissue parameters were measured including volumetric bone mineral density (vBMD, mg/cm$^3$), cross-sectional area (X-Area, mm$^2$), and bone mineral content (BMC, mg), using voxel dimensions of 148×148×1200 µm. Volume can be calculated by multiplying X-Area by the slice thickness of 1.2 mm. The entire femoral neck of excised femora in a bath of 50% ethanol, saline were scanned using a peripheral dual energy absorptiometry (pDEXA, Norland/Stratec). Specifically, apparent bone mineral density (aBMD, g/cm$^2$), projected area (cm$^2$) and bone mineral content (BMC, g) were measured using scan steps of 0.5×1.0 mm and threshold of 0.04.

Biomechanical Testing

Bone mechanical properties were measured in the right femoral midshaft and the body of L5. Bones were resected, cleaned of connective tissue, wrapped in gauze soaked in isotonic saline and frozen at −20° C. until testing. Prior to testing, specimens were thawed for 1-2 hours at room temperature. All specimens were tested to failure in a circulating water bath at 37° C. using an MTS 810 servo-hydraulic testing machine (MTS Corp., Minneapolis, Minn.). Load-deformation curves were recorded using the HP 7090A measurement plotting system (Hewlett Packard, Camas, Wash.). Ultimate force (maximum force that specimens sustain), stiffness (the slope of the linear portion of the load-deformation curve) and work to failure (area under the load-deformation curve before failure) were measured using a digitizer system (Jandel Scientific, Corte Madera, Calif.). These parameters are structural properties which depend on intrinsic material properties and geometry. Turner CH, Burr DB 1993 "Basic biomechanical measurements of bone: a tutorial." *Bone* 14:595-608. The data were normalized to obtain intrinsic material properties such as ultimate stress (maximum stress that specimens sustain), elastic modulus (material intrinsic stiffness), and toughness (resistance to fracture per unit volume) which are independent of size and shape. Id.

Femoral bone strength was measured at the midshaft using three-point bending. The femur was positioned on a fixture with the anterior side facing toward the loader. Load was applied on the mid-point between two supports that were 54 mm apart. The load cell was displaced at the rate of 1 mm/sec until failure occurred. To normalize the data obtained from the load-deformation curve, bending ultimate stress was calculated from ultimate force by $$\sigma_f = FuLr/8I \quad (1)$$

where $\sigma_f$ is bending fracture stress, Fu is the ultimate force, L is the length between supports, r is the radius in anterior-posterior direction, and I is the moment of inertia. Id. The value for the moment of inertia was calculated, assuming that the femoral cross-sections were elliptical.

Average cortical thickness was calculated from thickness measurements made in each of four quadrants of the femoral cross-section with a pair of digital calipers, accurate to 0.01 mm with a precision of ±0.005 mm (Mitutoyo, Japan).

Elastic modulus of the femur ($E_f$) was calculated using the following equation:

$$E_f = (\text{stiffness}) * (L^3/48I) \quad (2)$$

Toughness of the femur (Toughness$_f$) was also calculated using the following equation:

$$\text{Toughness}_f = 3 * (\text{work to failure}) * r^2/LI \quad (3)$$

For the mechanical testing of fifth lumbar vertebra (L5), both end plates of the vertebral body were cut parallel using a Buehler Isomet slow speed saw (Buehler LTD, Evanston, IL). After resection of the posterior processes, mechanical strength of L5 was measured in compression. The compressive load was applied in stroke control, with a cross-head speed of 1 mm/sec through a pivoting platen to correct for nonparallel alignment of the faces of the vertebral body. To normalize the data obtained from the load-deformation curve, and to evaluate intrinsic material properties that are independent of bone geometry, ultimate stress was calculated as the ultimate force divided by the gross cross-sectional area.

Cross-sectional area (CSA) was calculated by $$CSA = \pi ab/4 \quad (4)$$

where a and b are the width in the anterior-posterior and medial-lateral directions, respectively).

Elastic modulus of the vertebra ($E_v$) was calculated by $$E_v = (\text{stiffness})/(CSA/h) \quad (5)$$

where h is the cranio-caudal height of vertebral body.

Toughness of the vertebra (Toughness$_v$) was calculated by $$\text{Toughness}_v = (\text{work to failure})/(CSA*h) \quad (6)$$

Acoustic Microscopy

500-µm thick cross-sections were cut from the mid-diaphysis of the right humerus using a diamond wire saw. Precise thickness of each specimen was measured using a micrometer (Mitutoyo, Japan) at a resolution of 1 µm. Acoustic velocity measurements were made using a scanning acoustic microscope (UH3, Olympus, Japan) by the method described previously by Hasegawa K, Turner C H, Recker R R, Wu E, Burr D B 1995 "Elastic properties of osteoporotic bone measured by scanning acoustic microscopy". *Bone* 16:85-90. Using this technique, detailed intrinsic mechanical properties at a selected focal point can be measured. A 50 MHz transducer (V-390, Panametrics, Waltham, Mass.) was used to generate acoustic waves in pulse-echo mode. The 50 MHz lens produced an acoustic beam, approximately 60 µm in diameter. Specimens were fixed to the bottom of a chamber filled with water at constant temperature (22° C.). Delay time between acoustic waves reflected from the top of the specimens and those reflected from the bottom of the specimens was measured using a digital oscilloscope (TDS 620, Tekronix, Beaverton, Oreg.). Delay times were measured at five different locations such that each site was more than 300 µm from each other in the anterior cortex of the humerus. Acoustic velocity was calculated as twice the thickness of specimens, divided by the average delay time. Wet weight (Ww) and submerged weight (Ws) in 100% ethyl alcohol were measured using a balance (AJ100, Mettler Instrument Corp., Heightstown, N.J.). Wet density (ρ) was calculated using Archimedes's principle:

$$\rho = \{Ww/(Ww-Ws)\} * \rho ETOH \quad (7)$$

where $\rho ETOH$ is the density of alcohol (0.789 g/cm$^3$). Assuming the acoustic wave pathway in bone as homogenous, the elastic coefficient (C) representing the intrinsic stiffness of the specimens is calculated:

$$C = \rho * v^2 \quad (8)$$

where $\rho$ is wet density and v is acoustic velocity.

Statistical Analysis

Bartlett analysis was used to check homogeneity of variance. When variance was homogeneous, one-way ANOVA with Fisher's PLSD tests for post-hoc comparison was applied. When variance was not homogeneous, Kruskal-Wallis non-parametric analysis of variance was applied, with post-hoc analysis using Mann-Whitney's U-tests. Statistical significance was ascribed at p<0.05. Results are presented as mean ±SEM.

Results

Body Weight and Biochemistry

Rabbits treated with vehicle PTH(1-34) at 10 mg/kg/day exhibited minor increments in body weight over 140 days. Rabbits given PTH(1-34) at 40 µg/kg/day exhibited a small decrement of 51 g in body weight, representing a 1.4±1.6% loss in body weight during the experiment (Table 1). Serum measures were within the normal physiological response for rabbits, although small increases in serum calcium and urea nitrogen were observed. Serum alkaline phosphatase increased by 2-fold at the higher PTH(1-34) dose (Table 2).

TABLE 1

Effects of PTH(1-34) on Body Weight

|  | control | PTH(1-34) 10 µg/kg/day | PTH(1-34) 40 µg/kg/day |
| --- | --- | --- | --- |
| Initial body weight (kg) | 3.43 ± 0.08 | 3.42 ± 0.08 | 3.42 ± 0.08 |
| Final body weight (kg) | 3.70 ± 0.05 | 3.51 ± 0.05 | 3.37 ± 0.10 |
| Body weight gain (kg) | 0.26 ± 0.09 | 0.09 ± 0.05 | −0.05 ± 0.05* |

Data are expressed as mean ± SEM for 6 rabbits per group.
*P < 0.05 compared with control.

TABLE 2

Effects of PTH(1-34) on Serum Chemistry

|  | control | PTH(1-34) 10 µg/kg/day | PTH(1-34) 40 µg/kg/day |
| --- | --- | --- | --- |
| Calcium (mg/dl) | 12.1 ± 0.3 | 12.6 ± 0.2 | 13.5 ± 0.3* |
| Phosphate (mg/dl) | 4.7 ± 0.2 | 4.7 ± 0.2 | 5.5 ± 0.3 |
| Alkaline phosphatase (iu/l) | 24.7 ± 4.1 | 41.0 ± 8.1 | 49.8 ± 7.1* |
| Creatinine (mg/dl) | 1.9 ± 0.1 | 1.6 ± 0.1 | 1.8 ± 0.1 |
| Urea nitrogen (mg/dl) | 18.3 ± 0.3 | 18.1 ± 0.8 | 23.9 ± 1.9 |

Data are expressed as mean ± SEM for 6 rabbits per group.
*P < 0.05 compared with control.

Histomorphometry

Bone formation on periosteal (Ps.MS/BS) and endocortical (Ec.MS/BS) surfaces of the tibial midshaft increased in PTH(1-34) treated groups (Table 3). Ps.MS/BS in the higher dose group was significantly greater than in the other 2 groups (p<0.001) and Ec.MS/BS in the higher dose group was significantly greater than in the control group (p<0.05). Consistent with the increase in serum alkaline phosphatase, bone formation rates on each surface (Ps.BFR/BS and Ec.BFR/BS) were significantly greater in the higher dose group than the other 2 groups (p<0.05). Mineral apposition rate (MAR) did not change on either periosteal or endocortical envelopes.

Intracortically, the number of resorption sites (Rs.N/Ct.Ar) in rabbits given PTH(1-34) at 40 µg/kg/day was significantly greater by 7-fold, than in the other 2 groups (p<0.05) (Table 4). The number of labeled osteons (L.On.N/Ct.Ar) in rabbits given PTH(1-34) at 40 µg/kg/day also significantly increased compared to the other 2 groups (p<0.01 vs the control group, p<0.05 vs 10 µg/kg/day group). MAR was significantly greater in both treatment groups than in the control group (p<0.01), but there was no significant difference between the PTH-treated groups. Bone formation rate (BFR/BV) and activation frequency (Ac.F) increased (p<0.05 and p<0.01, respectively) at both doses.

Although bone area (B.Ar) increased at both doses, a significant difference was only found between the higher dose group and the control group (p<0.01). Marrow area (Ma.Ar) decreased after treatment, but was not significantly different among the three groups. However, cortical area (Ct.Ar) in the higher dose group was significantly greater than the other 2 groups (p<0.0001 vs the control group, p<0.05 vs the lower dose group). Ct.Ar in the lower dose group was also significantly higher than the control (p<0.05). Similar results were found in %Ct.Ar.

Cortical porosity (Ct.Po) in rabbits given PTH(1-34) at 10 µg/kg/day was double that in the control group (p<0.05), while Ct.Po in rabbits given PTH(1-34) at 40 µg/kg/day was 6× higher than the control group (p<0.01) However, porosities lay within the endocortical compartment and, within that location, are unlikely to contribute to biomechanical strength as PTH also increased cortical bone area, consistent with an increase in cross-sectional moment of inertia.

TABLE 3

Effects of PTH(1-34) on periosteal and endocortical bone remodeling of tibial midshaft.

| Parameters | Abbreviation | control | PTH(1-34) 10 µg/kg/day | PTH(1-34) 40 µg/kg/day |
| --- | --- | --- | --- | --- |
| Endocortical osteoid surface | Ec.OS/BS (%) | 8.8 ± 6.0 | 13.7 ± 10.5 | 20.2 ± 5.8 |
| Endocortical osteoid thickness | Ec.O.Th (µm) | 7.4 ± 2.4 | 3.7 ± 2.3 | 8.1 ± 0.9 |
| Periosteal mineral apposition rate | Ps.MAR (µm/day) | 0.33 ± 0.17 | 0.38 ± 0.08 | 0.66 ± 0.14 |

TABLE 3-continued

Effects of PTH(1-34) on periosteal and endocortical bone remodeling of tibial midshaft.

| Parameters | Abbreviation | control | PTH(1-34) 10 µg/kg/day | PTH(1-34) 40 µg/kg/day |
|---|---|---|---|---|
| Endocortical mineral apposition rate | Ec.MAR (µm/day) | 1.33 ± 0.22 | 0.79 ± 0.16 | 1.32 ± 0.15 |
| Periosteal mineralizing surface | Ps.MS/BS (%) | 3.8 ± 1.9 | 8.2 ± 2.1 | 22.3 ± 2.7*‡ |
| Endocortical mineralizing surface | Ec.MS/BS (%) | 26.4 ± 6.6 | 32.6 ± 8.2 | 57.7 ± 10.4* |
| Periosteal bone formation rate | Ps.BFR/BS ($\mu m^3/\mu m^2/yr$) | 0.02 ± 0.02 | 0.03 ± 0.01 | 0.16 ± 0.05*‡ |
| Endocortical bone formation rate | Ec.BFR/BS ($\mu m^3/\mu m^2/yr$) | 0.40 ± 0.10 | 0.31 ± 0.10 | 0.72 ± 0.12*‡ |

Data are expressed as mean ± SEM for 6 rabbits per group.
*P < 0.05 compared with control.
†P < 0.05 compared with PTH(1-34) 10 µg/kg/day.

TABLE 4

Effects of PTH(1-34) on intracortical bone remodeling of tibial midshaft.

| Parameters | Abbreviation | control | PTH(1-34) 10 µg/kg/day | PTH(1-34) 40 µg/kg/day |
|---|---|---|---|---|
| Resorption cavity number | Rs.N/Ct.Ar (#/mm$^2$) | 0.014 ± 0.013 | 0.013 ± 0.004 | 0.097 ± 0.036*‡ |
| Labeled osteon number | L.On.N/Ct.Ar (#/mm$^2$) | 0.011 ± 0.006 | 0.027 ± 0.006 | 0.215 ± 0.094*‡ |
| Osteoid thickness | O.Th (µm) | 4.92 ± 0.59 | 5.42 ± 0.30 | 5.16 ± 0.27 |
| Mineral apposition rate | MAR (µm/day) | 1.19 ± 0.20 | 1.56 ± 0.13* | 1.60 ± 0.12* |
| Bone formation rate | BFR/BV (%/yr) | 0.5 ± 0.3 | 8.5 ± 2.9* | 21.4 ± 3.8* |
| Activation frequency | Ac.F (#/mm$^2$/yr) | 1.8 ± 1.0 | 15.1 ± 5.0* | 43.8 ± 10.5*‡ |
| Bone area | B.Ar (mm$^2$) | 29.1 ± 1.3 | 33.3 ± 1.9 | 37.8 ± 2.7* |
| Marrow area | Ma.Ar (mm$^2$) | 12.7 ± 0.7 | 11.9 ± 1.0 | 10.7 ± 1.0 |
| Cortical area | Ct.Ar (mm$^2$) | 16.4 ± 0.9 | 21.3 ± 1.2* | 27.1 ± 2.0*‡ |
| % Cortical area | % Ct.Ar (%) | 56.4 ± 1.5 | 64.2 ± 1.6* | 71.6 ± 1.5* |

Data are expressed as mean ± SEM for 6 rabbits per group.
*P < 0.05 compared with control.
‡P < 0.05 compared with PTH(1-34) 10 µg/kg/day.

TABLE 5

Effects of PTH(1-34) on cancellous bone remodeling of third lumbar vertebra.

| Parameters | Abbreviation | control | PTH(1-34) 10 µg/kg/day | hPTH(1-34) 40 µg/kg/day |
|---|---|---|---|---|
| Bone volume | BV/TV (%) | 27.5 ± 1.4 | 30.5 ± 3.4 | 27.9 ± 3.2 |
| Trabecular thickness | Tb.Th (µm) | 124.8 ± 7.3 | 147.4 ± 12.7 | 126.4 ± 13.7 |
| Eroded surface | ES/BS (%) | 0.5 ± 0.3 | 1.4 ± 0.3 | 2.6 ± 0.7* |
| Osteoclast surface | Oc.S/BS (%) | 0.4 ± 0.2 | 0.9 ± 0.3 | 1.3 ± 0.3 |
| Osteoid surface | OS/BS (%) | 5.2 ± 1.3 | 7.2 ± 1.2 | 27.7 ± 3.8*‡ |
| Osteoblast surface | Ob.S/BS (%) | 1.4 ± 0.6 | 1.3 ± 0.6 | 15.3 ± 5.6*‡ |
| Osteoid thickness | O.Th (µm) | 5.2 ± 0.5 | 5.3 ± 0.5 | 4.4 ± 0.2 |
| Osteoid volume | OV/TV (%) | 0.10 ± 0.02 | 0.13 ± 0.03 | 0.46 ± 0.07*‡ |
| Mineral apposition rate | MAR (µm/day) | 1.3 ± 0.2 | 1.5 ± 0.1 | 1.7 ± 0.1 |
| Mineralizing surface | MS/BS (%) | 4.4 ± 1.4 | 7.4 ± 1.9 | 24.2 ± 1.5*‡ |
| Bone formation rate | BFR/BS ($\mu m^3/\mu m^2/yr$) | 19.7 ± 5.3 | 38.5 ± 8.9 | 153.0 ± 15.6*‡ |

Data are expressed as mean ± SEM for 6 rabbits per group.
*P < 0.05 compared with control.
‡P < 0.05 compared with PTH(1-34) 10 µg/kg/day.

In cancellous bone, most of the formation parameters (OS/BS, Ob.S/BS, OV/TV, and MS/BS) increased with PTH(1-34) treatment (Table 5). Those in rabbits given PTH(1-34) at 40 µg/kg/day were significantly greater than in the other 2 groups ($p<0.01$ vs both the control group and 10 µg/kg/day group in all parameters). Bone formation rate (BFR/BS) also significantly increased in rabbits given PTH (1-34) at 40 µg/kg/day compared to the other 2 groups ($p<0.0001$ vs both the control and 10 µg/kg/day,groups). Although, resorption (ES/BS and Oc.S/BS) increased in both PTH(1-34) treated groups, only eroded surface (ES/BS) in the higher dose group was significantly greater than the control group ($p<0.001$). There were no differences in osteoid thickness (O.Th) among the three groups. Despite the evidence for accelerated bone turnover, fractional bone volume (BV/TV) did not change after PTH(1-34) treatment. Tunneling resorption and peritrabecular fibrosis were not observed in any of the groups.

Bone Mass Measurements vBMD and BMC in the midshaft of the femur assessed by pQCT in 40 µg/kg/day group were significantly higher than in the other 2 groups ($p<0.001$ in vBMD and $p<0.0001$ in BMC vs the control group, p<0.05 in vBMD and p<0.01 in BMC vs the lower dose group) (FIG. 1A). vBMD and BMC in 10 μg/kg/day group were also significantly higher than in the control group (p<0.05 in both vBMD and BMC). Although bone area of the midshaft of the femur also increased dose-dependently, it significantly increased only in 40 μg/kg/day group (p<0.05).

aBMD and BMC in the proximal femur, measured by dual X-ray absorbtiometry (DXA or pDXA), increased dose-dependently. Significant differences were present in both aBMD and BMC between the control group and 10 μg/kg/day group (p<0.05) as well as between the control group and 40 μg/kg/day group (p<0.001) (FIG. 1B). No significant differences were found in bone area among the three groups.

Overall, FIG. 1 shows that BMD (bone mineral density) and BMC (bone mineral content) in the femoral midshaft (cortical bone) (A) and in the proximal femur (cancellous bone+cortical bone) (B) were significantly greater in PTH-treated animals than controls at both doses. Cortical bone area at the femoral midshaft in rabbits treated at the higher dose was significantly greater than controls. No significant differences were found between groups in bone area of the proximal femur. Data are expressed as mean ±SEM. *P<0.05 compared with the control. ‡P<0.05 compared with PTH 10 μg/kg/day.

There were no significant differences in vBMD, BMC or bone area of the lumbar vertebra (L4) assessed by pQCT, among the three groups.

Biomechanical Testing

Structural properties of the midshaft of the femur, such as ultimate force, stiffness and work to failure increased dose-dependently (FIG. 2). FIG. 2 shows the effects of PTH on mechanical strength and cross sectional moment of inertia (CSMI) in the cortical bone of the femoral midshaft. Structural mechanical properties (open bars) and CSMI increased significantly in the higher dose group, while stiffness also increased significantly in the lower dose group. Of the intrinsic material properties (dark bars), only elastic modulus increased significantly in the lower dose group when compared to controls. Elastic modulus in the higher dose group was significantly decreased when compared to the lower dose group. In FIG. 2: data are expressed as mean ±SEM; * indicates P<0.05 compared with the control; and ‡ indicates P<0.05 compared with 10 μg/kg/day.

In this study and the results shown in FIG. 2, all parameters were significantly higher in rabbits given PTH(1-34) at 40 μg/kg/day than in the control group (p<0.01 for ultimate force and work to failure, p<0.05 for stiffness). Stiffness in the lower dose group was also significantly higher than in the control group (p<0.05). Of the intrinsic material properties, elastic modulus was significantly less in rabbits given 40 μg/kg/day than those given 10 μg/kg/day (p<0.01).

In the lumbar vertebral body, no significant differences were found in mechanical properties among the three groups.

Acoustic Microscopy

There were no significant differences in acoustic velocity or elastic coefficient among the three groups.

Discussion

The skeletal response of cortical bone to biosynthetic hPTH(1-34) involved both a direct regulation of material properties and a compensatory regulation of biomechanical properties in the long bones of intact, mature female rabbits. PTH(1-34) increased bone turnover and cortical porosity and, at the 40 μg/kg dose, reduced the material elastic modulus of cortical bone. However, the decreased elastic modulus was more than compensated by increased bone apposition on periosteal and endocortical surfaces, resulting in a significant improvement in the structural strength, stiffness and work to failure of cortical bone in rabbits.

In this study using intact rabbits, cancellous bone volume of the lumbar vertebra did not change after PTH(1-34) treatment despite the evidence for increased bone turnover. Previous use as an osteopenic model, presence of intracortical remodeling, and short remodeling period—together with the rabbit's rapid growth and early skeletal maturation (by 6-9 months), formed the basis for selection of the rabbit as a model in which to test the effects of intermittently administered PTH(1-34).

Rabbits can exhibit a wide variation in serum calcium levels (10-16 mg/dl), but these levels are not directly influenced by the amount of dietary calcium, another advantage of the model. Although transient significant increases of approximately 1 mg/ml were recorded in rabbits treated with PTH(1-34) at 40 μg/kg, the actual values were always within the known physiologic range.

In the current study, biosynthetic hPTH(1-34) for 140 days increased bone formation rate intracortically as well as on periosteal and endocortical surfaces. Intracortical Ac.F increased in the lower dose group by 8× and in the higher dose group by 20×. This led to a 2-fold increase in cortical porosity in the tibia in the lower dose group and a 6-fold increase in the higher dose group. The data from acoustic microscopy shows that elastic properties of the bone material itself in the humerus was not affected, indicating that intrinsic cortical bone quality is normal. Therefore, the increased porosity must account for the slight reduction in elastic modulus, a material properties measurement that includes the spaces in the cortex.

Increased cortical porosity was more than compensated, however, by significantly increased MS/BS and BFR/BS on both periosteal and endocortical surfaces in the midshaft of the tibia in the higher dose group, resulting in significantly increased bone area. This would increase the cross-sectional moment of inertia, which is proportional to the bone's bending rigidity, as it did in the femoral midshaft (FIG. 2). The consequence of these changes in shape and material properties was to improve the mechanical strength and stiffness of the femoral diaphysis when compared to controls, thus offsetting the potentially deleterious mechanical effects of increased cortical porosity.

Conclusion

In conclusion, the increases in bone turnover and cortical porosity after PTH(1-34) treatment were accompanied by concurrent increases in bone at periosteal and endocortical surfaces. The combination of these phenomena resulted in an enhancement of the toughness ultimate stress, stiffness, and work to failure of the femur.

Example 2

Increased Bone Strength and Density Upon Administration of rhPTH(1-34) to Monkeys Experimental Procedures General The live phase of the study used feral, adult (closed growth plates) cynomolgus primates (Macaca fascicularis), weighing 2.77±0.03 kg (mean±standard error of the mean [SEM]). Monkeys were held in quarantine for 3 months, then started on a diet containing 0.3% calcium, 0.3% phosphate, and 250 IU vitamin D3/100 g diet, and given fluoridated water (1 ppm fluoride) ad libitum. The calcium content corresponded to 1734 mg calcium/2000 calories. After 1 month on the diet, animals were sorted into groups of 21 or 22, sham operated or ovariectomized. Once daily subcutaneous injections of vehicle (sham and ovariectomized controls) or rhPTH(1-34), at 1 μg/kg (PTH1) or 5 μg/kg (PTH5), were started 24 hours after ovariectomy. Animals were treated for either 18 months (PTH1 and PTH5), or for 12 months followed by withdrawal of treatment (PTH1-W and PTH5-W).

The study groups were divided as shown in Table 6.

TABLE 6

Study Groups for Primate Study

| Group | Abbreviation | Monkeys at Outset (n = 128) | Monkeys in Final Analyses (n = 121) |
|---|---|---|---|
| Sham ovariectomized, 18 months vehicle | Sham | 21 | 21 |
| Ovariectomized, 18 months vehicle | OVX | 22 | 20 |
| Ovariectomized, 18 months 1 μg rhPTH(1-34)/kg/day | PTH1 | 21 | 19 |
| Ovariectomized, 12 months 1 μg rhPTH(1-34/kg/day, 6 months vehicle | PTH1-W | 21 | 20 |
| Ovariectomized, 18 months 5 μg rhPTH(1-34)/kg/day | PTH5 | 22 | 21 |
| Ovariectomized, 12 months 5 μg rhPTH(1-34)/kg/day, 6 months vehicle | PTH5-W | 21 | 20 |

Serum and urinary samples were taken 24 hours after vehicle or rhPTH(1-34) injection at 3-month intervals. A sparse sampling design of 5 monkeys in each rhPTH(1-34)-treated group was used for pharmacokinetics, with sampling (spanning 0 to 240 minutes each time) at baseline, 7, 11, and 17 months. At 0 time and at 6-month intervals, total skeleton and spine (L-2 to L-4) bone mass were assessed by dual-energy x-ray absorptiometry (DXA); peripheral quantitative computed x-ray tomography (pQCT) was used to assess bone mass in the midshaft and distal radii, and the proximal tibia. Iliac biopsies were taken at 6 and 15 months for histomorphometry. All animals were euthanized after 18 months.

Biomechanical tests were done on lumbar vertebrae L-3 to L-4, the femur neck, humerus midshaft, and on a cortical bone specimen machined from the femur diaphysis (measures defined in Table 7). Conventional static and dynamic histomorphometry were done (measures described in Table 11) on the humerus midshaft, lumbar vertebra L-2, femoral neck, femur midshaft, the radius midshaft and distal radius. Initial statistical analyses compared all groups to vehicle-treated ovariectomized controls. The data is suitable for additional exploratory analyses to examine dose dependency, effects of withdrawal, interactions between outcomes, and changes in time by methods known to those of skill in the art. All assays were conducted and determined by methods known in the art.

For certain experimental subjects, cortical bone of the humerus was examined by histomorphometry and by polarized Fourier transform infrared microscopy. The Fourier transform infrared microscopy was conducted by an adaptation of known methods for such microscopy.

3D Finite Element Modeling Studies

These studies determined 3D finite element modeling data on vertebra from monkeys of the study dosed with PTH for 18 months. Excised L-5 vertebra in 50% ethanol/saline from the ovariectomized (n=7) and PTH (n=7) groups were serially scanned in 500 μm steps by quantitative computed tomography (QCT, Norland, Ft. Atkinson. Wis.), using 70×70 μm pixels. Each of the 500 μm cross-sections was analyzed for volumetric bone mineral density (BMD, mg/cc), bone mineral content (BMC, mg), cross-sectional area (X-Area), cancellous bone volume (BV/TV), trabecular thickness (Tb.Th), and connectivity (node density, strut analysis). Pixels in each serial scan were averaged to create 490×490×500 μm voxels. The serial scans were then stacked and a triangular surface mesh generated for each bone using the "marching cubes" algorithm (see e.g. Lorensen and Cline 1987 "Marching cubes, a high resolution 3D surface construction algorithm." *Computer Graphics* 21, 163-169).

A smoothed version of each surface mesh was then used to generate a tetrahedral mesh for 3D finite-element modeling.

Young's modulus for each tetrahedral element was derived from the original voxel densities and material properties from a beam of cortical bone milled from the femoral diaphysis of the monkeys. Each tetrahedral mesh was rotated so that the bottom surface of each vertebra was aligned with a plane. Linear elastic stress analysis was then performed for each L-5 model in which a distributed load of 100 N was applied to the top surface of the centrum, perpendicular to the bottom plane while the bottom surface was fixed in the direction of loading. The resulting axial strain contours were evaluated, as were the BMD distributions, and compared between PTH and ovariectomized. At this resolution, the density of each voxel is dependent on the extent to which each voxel is filled with bone as opposed to soft tissue.

Results

Reports of differences in the text are statistically significant, $p<0.05$. All animals gained 4% to 9% of initial body weight during the study independent of treatment.

Serum and Urine Measures

Serum estradiol levels at 3 and 18 months were below 5 pg/mL in all ovariectomized monkeys. When measures of calcium homeostatis were compared to sham controls, ovariectomized controls had lower serum calcium and phosphate and 1,25-dihydroxyvitamin D levels, but did not differ in endogenous PTH, urinary cyclic adenosine monophosphate (cAMP), urinary calcium, urinary creatinine, or serum urea nitrogen measured 24 hours after last injection. Animals treated with rhPTH(1-34) had lower serum phosphate, lower endogenous PTH, and higher 1,25-dihydroxyvitamin D and urinary cAMP compared to ovariectomized. Serum bone formation marker assays showed that ovariectomized monkeys had low serum total alkaline phosphatase (ALP) and osteocalcin compared to shams, and rhPTH(1-34) restored levels back to sham values. Urinary C-telopeptide (CrossLaps) excretion, used as a biochemical marker of bone resorption, was not altered by rhPTH(1-34) compared to ovariectomized controls.

Bone Mass

Figure 3:
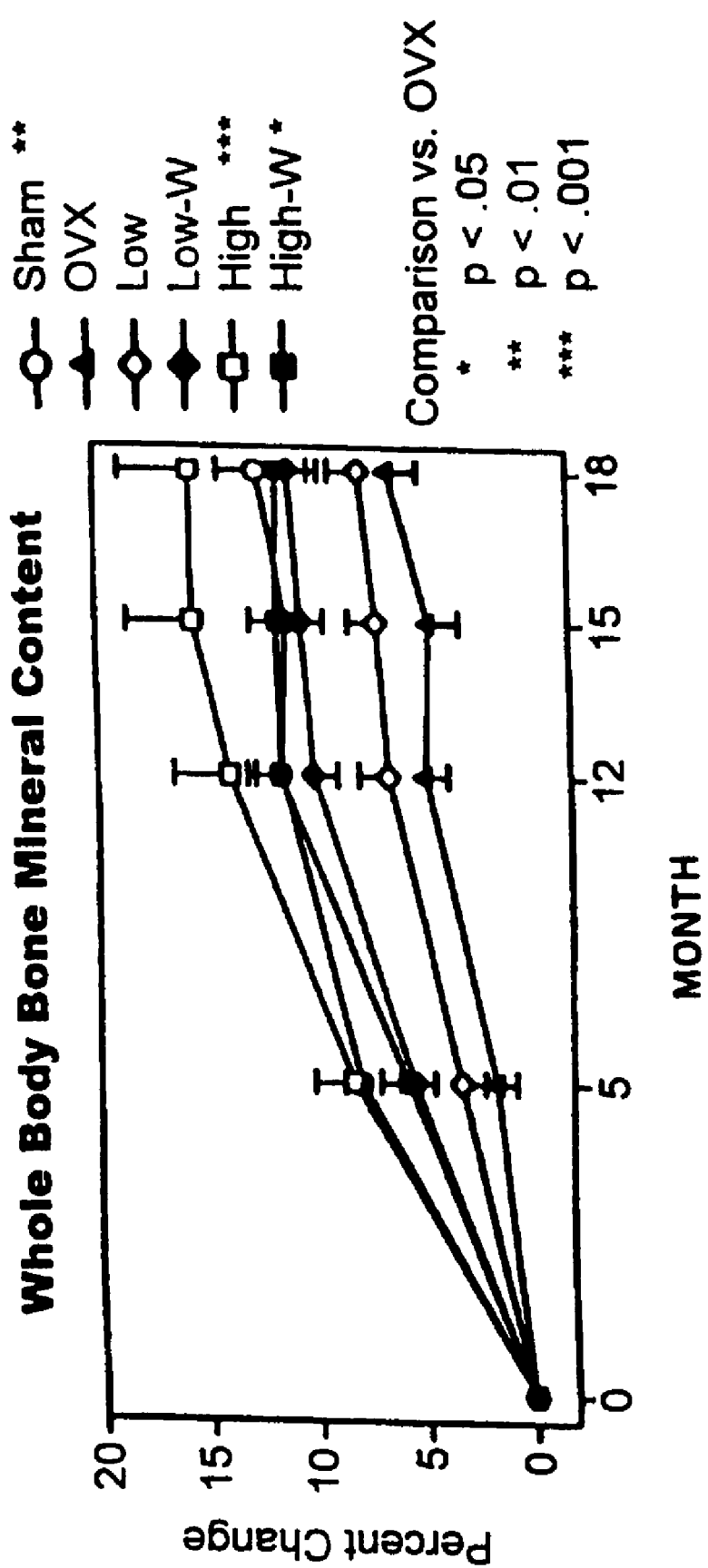
FIG. 3 illustrates the percent change in DXA measures of whole bone mineral content in control and treatment groups.
Figure 4A:
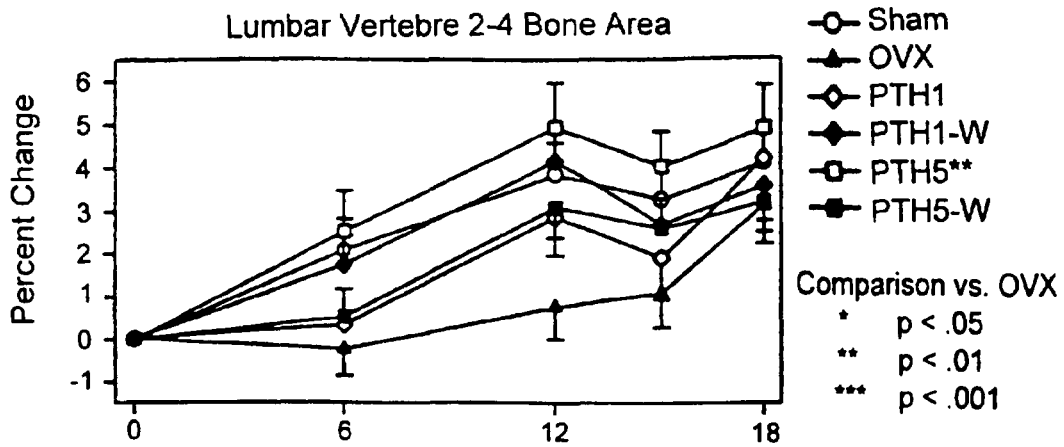
FIGS. 4A-C illustrate the percent change in DXA measures of the spine for control and treatment groups in the lumbar vertebrae 2-4 for bone area (A), bone mineral content (B), and bone mineral density (C).
Figure 4B:
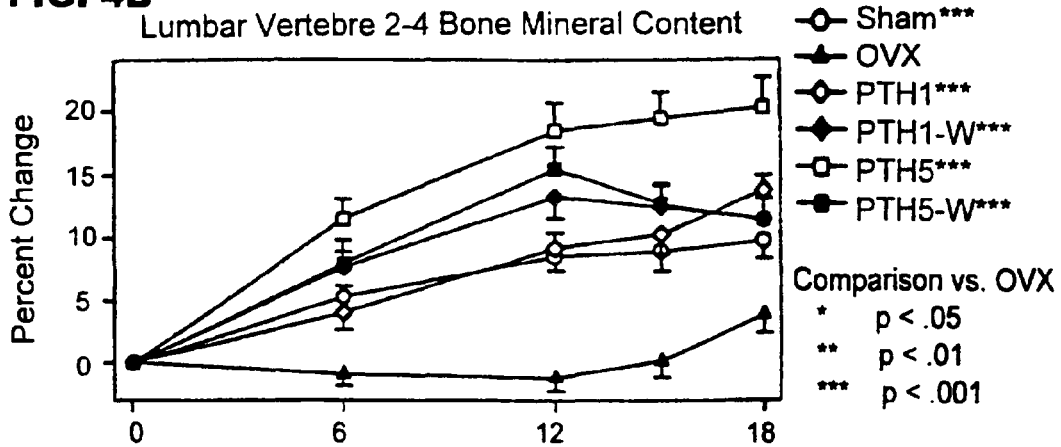
Figure 4C:
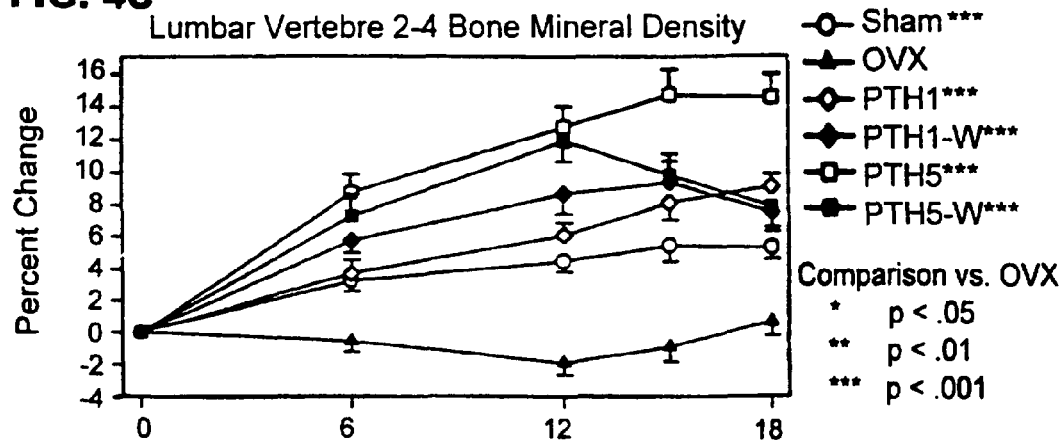

Overall skeletal bone mass, expressed as total body BMC, was increased significantly by PTH(1-34) (FIG. 3). Spine bone mineral density (BMD) remained stable in ovariectomized controls for 18 months, while sham controls gained approximately 5% above baseline (FIGS. 4A-4C and 5A). rhPTH(1-34) increased spine BMD by 7% to 14% and whole body bone mineral content (BMC, FIG. 3) by up to 6% compared to baseline (FIGS. 4A-4C and 5A). Spine bone mineral content also increased (FIG. 5A). in rhPTH (1-34)-treated primates, the magnitude of these increases was significantly higher than that of ovariectomized controls, and matched (PTH1) or exceeded (PTH5) that of shams. rhPTH(1-34) did not alter BMD of the midshaft or distal radius. The cross-sectional area of the midshaft increased by 7% in the PTH5 group. In the proximal tibia, there was no increase in cross-sectional area but rhPTH(1-34) increased BMC and BMD compared to ovariectomized controls. Six months after treatment was withdrawn, BMD and BMC in the spine and femur neck remained higher than ovariectomized controls, with no change in the cortical midshaft of the humerus.

Figure 5B:
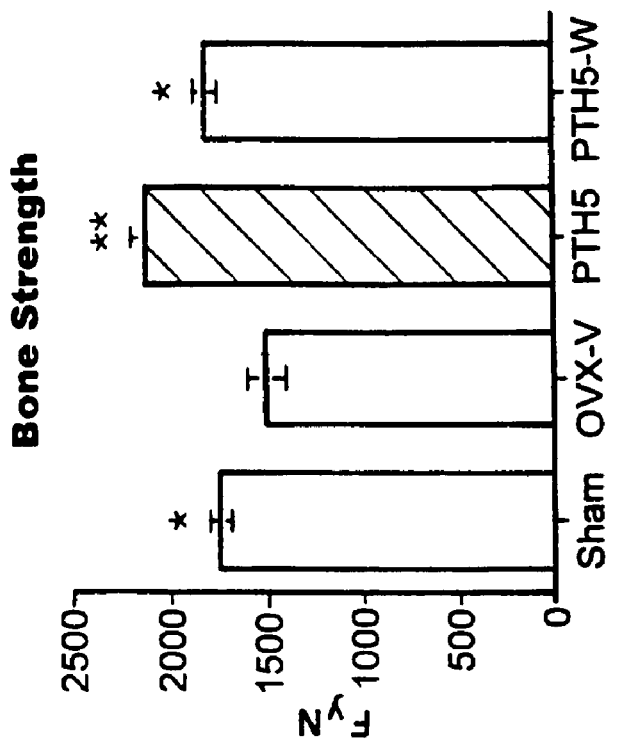
FIGS. 5A and 5B illustrate the increase in bone mass (A) and bone strength (B) in lumbar vertebrae of primates treated with a parathyroid hormone.
Figure 5A:
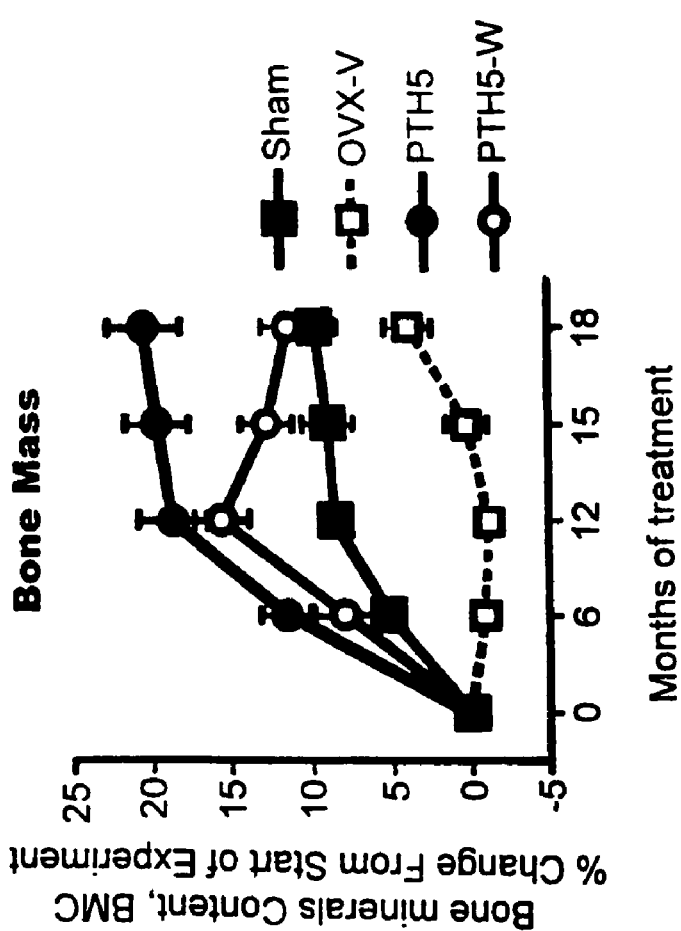
Figure 6B:
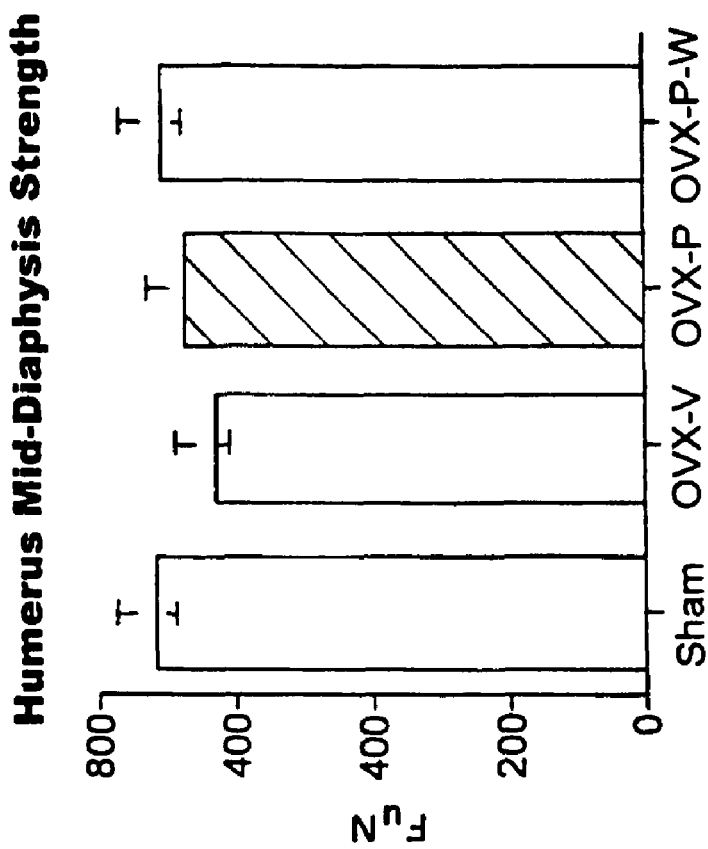
FIGS. 6A and 6B illustrate the increase in strength of femur neck (A) and the constant strength of humerus mid-diaphysis (B) in primates treated with a parathyroid hormone.
Figure 6A:
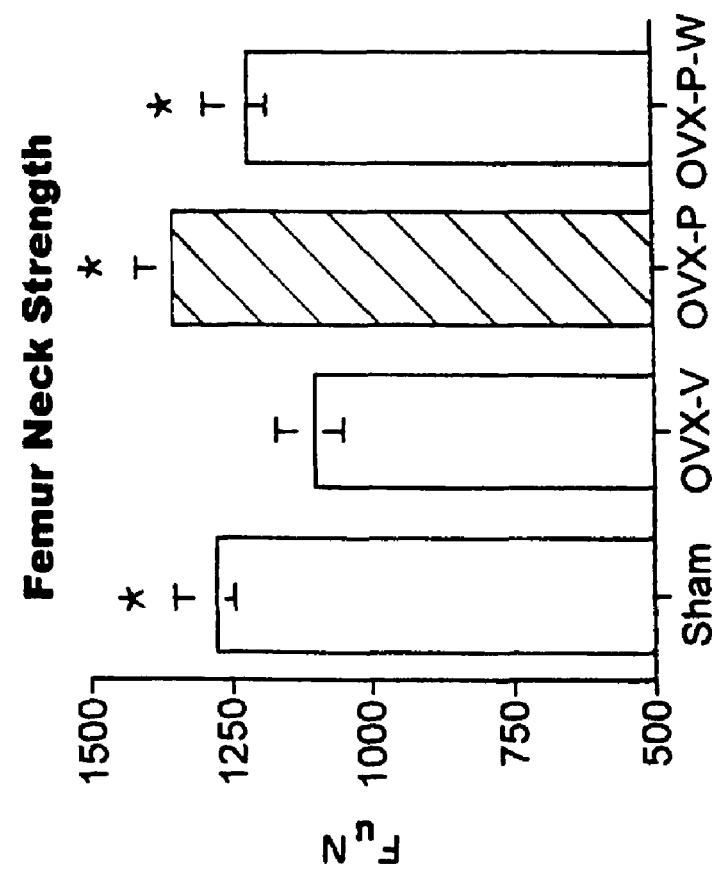

Bone Strength rhPTH(1-34) increased strength ($F_y$) in the vertebrae by up to 43% (Tables 7 and 8, FIG. 5B). rhPTH(1-34) improved strength in the femur neck ($f_u$) by up to 12% (Tables 7 and 9, FIG. 6A). rhPTH(1-34) did not alter measures in the cortical diaphysis of the humerus midshaft (Tables 7 and 10), or the material properties of beam specimens machined from the femoral diaphysis (Tables 7 and 9, FIG. 6B) when compared to ovariectomized controls. In animals treated with rhPTH(1-34) for 12 months and then withdrawn from treatment for 6 months, bone strength measures remained significantly higher than ovariectomized controls (Tables 7-10, FIGS. 5B and 6A).

TABLE 7

Variables Reported for the Third and Fourth Lumbar Vertebrae (L-3 and L-4), Humerus Midshaft, Proximal Femoral Neck, and Femoral Beam Specimens

| Variable | Units | Description |
|---|---|---|
| Lumbar Vertebrae, L-3 and L-4 | | |
| A | mm² | Cross-sectional area |
| F | N | Yield force is the force at a 0.2% offset |
| S | N/mm | Slope of the linear portion of the force-displacement curve (stiffness) |
| σy | Mpa | Yield stress |
| E | Mpa | Young's modulus |
| Humerus Midshaft | | |
| t | mm | Average cortical thickness |
| $F_u$ | N | Ultimate force is the maximum force the specimen can withstand |
| S | N/mm | Slope of the linear portion of the force-displacement curve (stiffness) here's stiffness |
| mJ/U | N-mm | Area under the load-displacement curve (U = work to failure) |
| Proximal Femoral Neck | | |
| $F_u$ | N | Ultimate force is the maximum force the specimen can withstand |
| Femur Diaphysical Beam Specimens | | |
| $\sigma_u$ | Mpa | Ultimate stress |
| E | Gpa | Young's modulus |
| u | J/m³ | Toughness |
| $\epsilon_u$ | | Ultimate strain |

TABLE 8

Biomechanical Measures of Strength in the Spine (Lumbar Vertebrae, L-3 and L-4 Combined) of Ovariectomized Primates at 18 Months

| Variable (units)[a] | Sham | OVX Control | PTH1 | PTH1-W | PTH5 | PTH5-W |
|---|---|---|---|---|---|---|
| A (mm²) | 90.5 ± 2.1[b] | 86.7 ± 2.3 | 88.3 ± 2.0 | 90.9 ± 2.3 | 87.3 ± 2.7 | 82.8 ± 2.1 |
| $F_y$ (N) | 1738 ± 52 | 1499 ± 94[s] | 1915 ± 105° | 1899 ± 73° | 2113 ± 77[s,o] | 1792 ± 59° |
| S (N/mm) | 7312 ± 319 | 5805 ± 476[s] | 7701 ± 476° | 7401 ± 452° | 8012 ± 367° | 7074 ± 314° |
| $\sigma_y$ (Mpsa) | 19.4 ± 0.6 | 17.3 ± 1.0 | 21.9 ± 1.3° | 21.1 ± 0.8° | 24.6 ± 1.1[s,o] | 21.9 ± 0.9° |
| E (Mpa) | 650 ± 32 | 546 ± 49 | 717 ± 48° | 659 ± 42 | 759 ± 36° | 698 ± 41° |

Abbreviations:
OVX = ovariectomized;
PTH1 = rhPTH(1-34) 1 μg/kg for 18 months;
PTH1-W = withdrawal for 6 months after treatment with rhPTH(1-34) 1 μg/kg for 12 months;
PTH5 = rhPTH(1-34) 5 μg/kg for 18 months;
PTH5-W = withdrawal for 6 months after treatment with rhPTH(1-34) 5 μg/kg for 12 months.
[a]See Table 4.1 for description of variables
[b]Data expressed as mean ± standard error of the mean (SEM) per group.
°Statistically significant compared to OVX controls (p < 0.05).
[s]Statistically significant compared to sham controls (p < 0.05).

TABLE 9

Biomechanical Measures of Material Properties of Equivalent Size Beam Specimens from Femur Diaphysis, and Biomechanical Measure of Strength of Femur Neck of Ovariectomized Primates at 18 Months

| Variable (units)[a] | Sham | OVX Control | PTH1 | PTH1-W | PTH5 | PTH5-W |
|---|---|---|---|---|---|---|
| $\sigma_u$ (Mpa) | 222 ± 5[b] | 216 ± 5 | 222 ± 4 | 214 ± 6 | 206 ± 6 | 208 ± 6 |
| E (Gpa) | 17.2 ± 0.6 | 16.4 ± 0.4 | 17.1 ± 0.4 | 16.6 ± 0.6 | 15.4 ± 0.6[s] | 15.3 ± 0.6[s] |
| u (mJ/m³) | 5.9 ± 0.3 | 5.8 ± 0.4 | 6.1 ± 0.4 | 5.5 ± 0.4 | 5.4 ± 0.4 | 6.1 ± 0.4 |
| $\epsilon_u$ | 0.035 ± 0.001 | 0.035 ± 0.002 | 0.036 ± 0.002 | 0.034 ± 0.002 | 0.034 ± 0.002 | 0.038 ± 0.002 |
| Proximal femur neck | | | | | | |
| $F_u$ | 1288 ± 41 | 1105 ± 53[s] | 1235 ± 45[o] | 1258 ± 52[o] | 1362 ± 30[o] | 1213 ± 42 |

Abbreviations:
OVX = ovariectomized;
PTH1 = rhPTH(1-34) 1 µg/kg for 18 months;
PTH1-W = withdrawal after treatment with rhPTH(1-34) 1 µg/kg for 12 months;
PTH5 = rhPTH(1-34) 5 µg/kg for 18 months;
PTH5-W = withdrawal after treatment with rhPTH(1-34) 5 µg/kg for 12 months.
[a]See Table 4.1 for description of variables
[b]Data expressed as mean ± standard error of the mean (SEM) per group.
[o]Statistically significant compared to OVX controls ($p < 0.05$).
[s]Statistically significant compared to sham controls ($p < 0.05$).

TABLE 10

Biomechanical Measures of Cortical Bone of the Midshaft of the Humerus of Ovariectomized Primates at 18 Months

| Variable (units)[a] | Sham | OVX Control | PTH1 | PTH1-W | PTH5 | PTH5-W |
|---|---|---|---|---|---|---|
| t(mm) | 1.74 ± 0.04[b] | 1.63 ± 0.03[s] | 1.68 ± 0.03 | 1.66 ± 0.04 | 1.80 ± 0.04[o] | 1.72 ± 0.05 |
| $F_u$(N) | 725 ± 26 | 636 ± 26 | 654 ± 23 | 689 ± 23 | 680 ± 15[s] | 707 ± 24 |
| S(N/mm) | 601 ± 23 | 520 ± 26 | 544 ± 23 | 573 ± 20 | 548 ± 18 | 573 ± 24 |
| U(mJ) | 1797 ± 85 | 1542 ± 92 | 1641 ± 137 | 1751 ± 84 | 1804 ± 99 | 1775 ± 113 |

Abbreviations:
OVX = ovariectomized;
PTH1 = rhPTH(1-34) 1 µg/kg for 18 months;
PTH1-W = withdrawal after treatment with rhPTH(1-34) 1 µg/kg for 12 months;
PTH5 = rhPTH(1-34) 5 µg/kg for 18 months;
PTH5-W = withdrawal after treatment with rnPTH(1-34) 5 µg/kg for 12 months.
[a]See Table 4.1 for description of variables
[b]Data expressed as mean ± standard error of the mean (SEM).
[o]Statistically significant compared to OVX controls ($p < 0.05$).
[s]Statistically significant compared to sham controls ($p < 0.05$).

Bone Histomorphometry

Although turnover rates were greater in ovariectomized than sham controls, there was no significant loss of bone volume in the iliac crest. As the tetracycline label given at 6 months was not detectable in many animals, only static parameters were measured for this time point. Static and dynamic histomorphometry data at 15 months showed that treatment with rhPTH(1-34) increased cancellous bone area compared to ovariectomized, and increased bone formation without increasing resorption measures above those measured in ovariectomized controls. Bone formation rate was increased progressively by higher doses of rhPTH(1-34). Although cancellous bone remained increased compared to ovariectomized controls after withdrawal of rhPTH(1-34) following 12 months of treatment, bone formation and resorption reverted to that seen in ovariectomized controls, and bone turnover remained higher than in sham controls. rhPTH(1-34) did not affect mineralization, activation frequency, or remodeling periods. There were no differences in individual bone multicellular unit (BMU)-based bone balance between resorption and formation. In summary, rhPTH (1-34) increased cancellous bone by selective stimulation of bone formation.

In the cortical bone of the humerus, where rhPTH(1-34) did not significantly modify BMD or bone strength measures, rhPTH(1-34) stimulated changes in the periosteal, endosteal, and intracortical compartments (Tables 11 and 12). Although there were no differences in total area or medullary area between groups, rhPTH(1-34) increased cortical area, and the PTH5 and PTH5-W groups had significantly more cortical bone, suggestive of increased cross-sectional moment of inertia, a measure of strength. The increase in area could be attributed to increased formation on both periosteal and endosteal surfaces (FIG. 7).

Sham controls and PTH5-W groups had reduced periosteal mineralizing surfaces compared to ovariectomized controls and the other rhPTH(1-34)-treated groups. Endocortical mineralizing surfaces were significantly greater in ovariectomized controls compared to shams and rhPTH(1-34) did not increase above ovariectomized control values. In intracortical remodeling, there were more resorption spaces in ovariectomized animals, and activation frequency was greater in ovariectomized, PTH1, and PTH5 groups than in sham controls or either of the withdrawal groups. There were significantly more labeled osteons per unit area in ovariectomized compared to sham controls, and rhPTH(1-34) did not increase these significantly above ovariectomized control values.

Intracortical porosity was greater in ovariectomized compared to shams, but not different between ovariectomized controls and PTH1. PTH5 and PTH5-W increased porosity above that seen in ovariectomized controls. Data from the rabbit studies suggested the hypothesis that the increase in porosity, accompanied by increased cortical bone, may be a structural response to maintain the biomechanical properties of rhPTH(1-34)-treated bone. There were no differences between ovariectomized and the other groups in formation period, osteoid width, wall width, or osteoid maturation at 18 months.

In summary, there were no differences in turnover rates between ovariectomized controls and either dose of rhPTH (1-34). Sham controls had a lower turnover rate than either ovariectomized controls or rhPTH(1-34)-treated animals. When rhPTH(1-34) was withdrawn for 6 months, turnover rates decreased significantly, but BMD and biomechanical strength measures remained higher than ovariectomized controls. Normal values for osteoid width and maturation time intracortically for all groups indicates treatment did not cause any defect in the normal timing of the mineralizing process. Normal values for wall width indicate that treatment did not alter the normal balance between resorption and formation at the level of the individual BMU.

TABLE 11

Histomorphometric Variables for Cortical Bone Measurements of the Humerus

| Variable[a] | Units | Description |
|---|---|---|
| Ac F | cycles/year | Activation frequency |
| BFR/BS Ec | μm/day | Bone formation rate, endocortical surface referent |
| BFR/BS.Ps | μm/day | Bone formation rate, periosteal surface referent |
| BFR/BV | %/year | Bone formation rate, bone volume referent |
| FP | days | Formation period |
| L On N/Ct A | #/mm$^2$ | Number of fluorochrome labeled osteons per unit cortical area |
| MAR | μm/day | Mineral apposition rate, intracortical |
| MAR Ec | μm/day | Mineral apposition rate, endocortical surface |
| MAR Ps | μm/day | Mineral apposition rate, periosteal surface |
| MS/BS.Ec | % | Mineralizing endocortical surface normalized to total endocortical surface |
| MS/BS.Ps | % | Mineralizing periosteal surface normalized to total periosteal surface |
| O W$_1$ | μm | Osteoid width |
| Rs N/Ct A | #/mm$^2$ | Number of resorption spaces per unit cortical area |
| W W$_1$ | μm | Osteonal wall width |
| omt | days | Osteoid maturation time |
| Po | % | Porosity, the percentage of bone area occupied by spaces |
| B Ar | mm$^2$ | Bone area, the total area within the periosteal surface |
| Ct Ar | mm$^2$ | Cortical area, the area of bone within the periosteal surface (includes porosities) |
| Mc Ar | mm$^2$ | Medullary cavity area |

[a]Nomenclature is that recommended in Journal of Bone and Mineral Research, 1987.

TABLE 12

Cortical Histomorphometry of the Humerus Midshaft of Ovariectomized Primates at 18 Months (n = 121)

| Variable[b] | Sham | OVX | PTH1 | PTH1-W | PTH5 | PTH5-W |
|---|---|---|---|---|---|---|
| Ac.F | 1.85 ± 1.87[a,c] | 6.06 ± 3.31 | 7.69 ± 4.96 | 3.05 ± 2.15[a] | 8.70 ± 3.97 | 2.05 ± 1.46[a] |
| BFR/BS.Ec | 7.08 ± 3.80 | 20.93 ± 19.23 | 18.14 ± 13.95 | 14.89 ± 10.32 | 34.04 ± 19.01 | 12.73 ± 16.33[a] |
| BFR/BS.Ps | 3.79 ± 3.07 | 9.12 ± 7.58 | 8.53 ± 10.54 | 3.60 ± 3.84[a] | 8.99 ± 5.81 | 5.79 ± 4.05 |
| BFR/BV | 2.13 ± 2.06[a] | 9.16 ± 5.37 | 9.23 ± 5.93 | 4.39 ± 3.48[a] | 12.93 ± 5.94[a] | 2.21 ± 1.73[a] |
| FP | 82.73 ± 41.06 | 65.94 ± 19.79 | 63.44 ± 10.02 | 64.94 ± 11.99 | 81.97 ± 95.63 | 88.63 ± 52.90 |
| L.On.N/Ct.A | 0.28 ± 0.27[a] | 1.03 ± 0.52 | 1.26 ± 0.71 | 0.50 ± 0.36[a] | 1.45 ± 0.47[a] | 0.38 ± 0.26[a] |
| MAR | 0.91 ± 0.33[a] | 1.07 ± 0.19 | 0.98 ± 0.12[a] | 1.06 ± 0.27 | 1.03 ± 0.23 | 0.85 ± 0.28[a] |
| MAR.Ec | 0.48 ± 0.19[a] | 0.75 ± 0.25 | 0.66 ± 0.15 | 0.66 ± 0.16 | 0.75 ± 0.14 | 0.63 ± 0.17 |
| MAR.Ps | 0.62 ± 0.24 | 0.69 ± 0.23 | 0.89 ± 0.95 | 0.54 ± 0.15[a] | 0.66 ± 0.17 | 0.82 ± 0.15 |
| MS/BS.Ec | 3.09 ± 6.49[a] | 20.99 ± 18.04 | 25.19 ± 17.14 | 11.74 ± 14.41[a] | 40.47 ± 24.68[a] | 8.93 ± 15.39[a] |
| MS/BS.Ps | 1.81 ± 3.59[a] | 10.03 ± 10.49 | 8.59 ± 5.73 | 3.86 ± 4.83[a] | 11.00 ± 9.63 | 2.30 ± 3.76[a] |
| O.Wi | 3.77 ± 0.92 | 4.04 ± 0.91 | 3.66 ± 0.67 | 3.96 ± 0.83 | 3.94 ± 1.13 | 3.76 ± 0.83 |
| Rs.N/Ct.A | 0.12 ± 0.17[a] | 0.21 ± 0.13 | 0.28 ± 0.18 | 0.12 ± 0.07[a] | 0.43 ± 0.26[a] | 0.19 ± 0.18 |
| W.Wi | 63.23 ± 13.61 | 68.63 ± 15.09 | 61.36 ± 7.79 | 63.12 ± 17.35 | 65.28 ± 9.43 | 63.82 ± 8.31 |
| omt | 4.58 ± 1.26[a] | 3.87 ± 1.04 | 3.76 ± 0.70 | 3.86 ± 0.74 | 6.45 ± 13.85 | 5.07 ± 2.65 |
| Po | 1.32 ± 0.60[a] | 2.61 ± 1.40 | 4.65 ± 4.78 | 2.23 ± 1.60 | 6.78 ± 4.23[a] | 6.40 ± 4.22[a] |
| B.Ar | 53.12 ± 5.50 | 52.82 ± 7.09 | 54.22 ± 5.97 | 54.94 ± 6.55 | 55.81 ± 6.24 | 58.16 ± 8.79[a] |

TABLE 12-continued

Cortical Histomorphometry of the Humerus Midshaft of Ovariectomized Primates at 18 Months (n = 121)

| Variable[b] | Sham | OVX | PTH1 | PTH1-W | PTH5 | PTH5-W |
|---|---|---|---|---|---|---|
| Ct.Ar | 37.40 ± 3.75 | 35.35 ± 5.04 | 37.61 ± 3.86 | 38.10 ± 4.83 | 40.96 ± 4.30[a] | 40.83 ± 5.80[a] |
| Me.Ar | 15.72 ± 4.07 | 17.47 ± 4.22 | 16.61 ± 3.77 | 16.84 ± 3.74 | 14.85 ± 4.72[a] | 17.34 ± 6.05 |

Abbreviations:
OVX = ovariectomized;
PTH1 = rhPTH(1-34) 1 μg/kg for 18 months;
PTH1-W = withdrawal after treatment with rhPTH(1-34) 1 μg/kg for 12 months;
PTH5 = rhPTH(1-34) 5 μg/kg for 18 months;
PTH5-W = withdrawal after treatment with rhPTH(1-34) 5 μg/kg for 12 months.
[a]Statistically significant compared to OVX controls (p < 0.05).
[b]See table 4.2 for description of variables.
[c]Data are expressed as mean ± standard error of the mean (SEM).

The analysis by histomorphometry and polarized Fourier transform infrared microscopy revealed that administration of PTH improved bone quality by replacing old bone (large crystallites) with young bone (range of sized crystallites, tending to smaller size). Further, upon withdrawal of PTH from monkeys given low doses, there is an additional benefit as the matrix becomes optimally mineralized, and the crystallites mature. The data derived from histomorphometry and Fourier transform infrared microscopy show an unexpected benefit on bone quality of the cortical bone as optimal mineralization occurs the mineral phase matures.

3D Finite Element Modeling Studies

Examination of the middle 500 μm slice of L-5 showed a 21% increase in BMD for PTH compared to ovariectomized that was due to a 27% increase in BMC with no change in the cross sectional area. Analysis of the centrum from PTH showed a 73% increase in BV/TV that was due to a 30% increase in Tb.Th and 37% greater Tb.N, compared to ovariectomized. Connectivity analysis for this region showed a 140% greater node density (node/tissue volume) and 286% greater node-to-node struts for the PTH vertebra.

Figure 8:
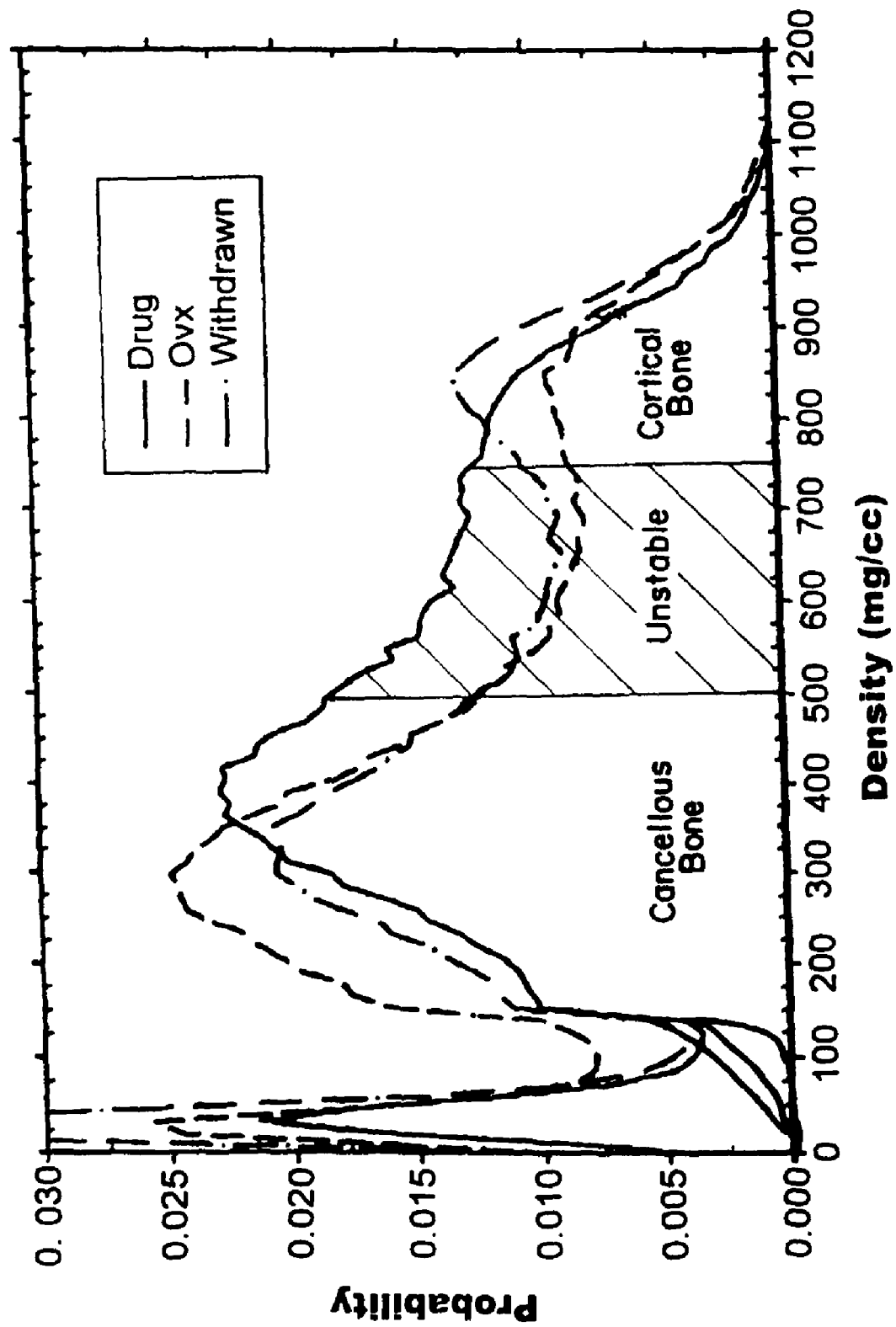
FIG. 8 illustrates the histogram analysis of the shift in bone voxel densities in lumbar vertebra, resulting from PTH treatment compared to control. Note the increase in density in cortical bone compartment after withdrawal of PTH treatment.

Histogram distribution analysis of bone voxel densities for PTH showed a decrease in the proportion of low densities (0-355 mg/cc), an increase in middle densities (356-880 mg/cc), with little effect on the high density voxels (887-1200 mg/cc), compared to ovariectomized (FIG. 8). Most striking was the shift to a greater bone voxel density in the cortical bone compartment following withdrawal of treatment for 6 months (FIG. 8).

The proportion of vertebral bone elements (voxels) that fell within a certain range of BMD values was calculated. The BMD ranges chosen were the following: low BMD, 0-300 mg/cc; medium BMD, 300-700 mg/cc; high BMD, 700-1000 mg/cc; and cortical BMD, >1000 mg/cc (Table 13). Compared to ovariectomized controls, PTH treatment significantly decreased the volume of low BMD bone and increased the volume of medium BMD bone. After withdrawal of PTH, there was a decrease in medium BMD bone and an increase in high BMD bone, indicating that medium BMD bone became more dense.

TABLE 13

Percentages of L5 vertebral volume grouped by BMD values (mean ± SEM)

| Treatment | low BMD (%) | medium BMD (%) | high BMD (%) | cortical BMD (%) |
|---|---|---|---|---|
| ovariectomized | 30.4 ± 2.2 | 48.7 ± 1.6 | 19.9 ± 1.2 | 0.9 ± 0.3 |
| PTH | 17.7 ± 1.6* | 58.9 ± 1.9* | 22.8 ± 2.7 | 0.6 ± 0.3 |
| PTH-W | 22.4 ± 1.3* | 49.7 ± 1.2 | 27.0 ± 1.6* | 0.8 ± 0.2 |

TABLE 14

BMC at the midlevel of the L5 vertebra and vertebral effective strain

| Treatment | BMC (mg) | effective strain (ustrain) |
|---|---|---|
| ovariectomized | 37.2 ± 1.6 | 701 ± 64 |
| PTH | 47.4 ± 1.5* | 447 ± 36* |
| PTH-W | 44.2 ± 1.2* | 539 ± 34* |

*statistically different (p < 0.05 by Fisher's PLSD test)

The data summarized in FIG. 8 show that L-5 vertebra from cynomolgus monkeys treated for 18 months with PTH respond with significant increases in bone mass, trabecular thickness, and trabecular connectivity, with marginal effects on the outer dimensions (X-Area) of the vertebra. Analysis of the distribution of bone elements in L-5 showed that the heavily mineralized bone regions change the least with no evidence of bone sclerosis. Rather, it is the porous trabecular bone that responded the most to PTH. The shift in BMD led to a substantial reduction in the axial strain, indicating mechanical improvement, As clearly shown in the histograms of PTH and ovariectomy BMD, PTH converted the low density bone voxels into medium density voxels with no significant effect on the high density voxels.

The data summarized in Table 2 show that the BMC through the middle of the vertebrae was significantly increased by PTH treatment and a beneficial effect of PTH remained after 6 months of withdrawal. The average mechanical strain in the vertebra was reduced 36% by PTH treatment and remained 23% below OVX after withdrawal of PTH. This study indicates that withdrawal of PTH treatment for 6 months did not lead to resorption of newly formed bone, but instead there was a beneficial redistribution of medium density bone into lower and higher density bone. This redistribution led to continued strain reduction in the vertebrae and thus improved mechanical function.

Discussion

This primate study indicates that PTH, given in the absence of other medicines that might affect bone, benefits both cortical and trabecular bone to increase overall skeletal bone mass. Moreover, withdrawal of PTH did not result in significant loss of benefits associated with PTH treatment over a period of at least 2 remodeling cycles.

Surrogate markers have been used in other trials to indicate activity in bone, and they assumed that changes in value reflect changes in bone mass. Although there are published data on humans and primates to show that both formation and resorption markers increase, consistent with activation of bone turnover, for example, during early menopause or in active disease states, the high turnover is considered to be indicative of bone loss. In adolescence, high turnover during maturation of the human skeleton has been less well studied, but is accompanied by an anabolic gain in bone mass. Such a phenomenon would be totally unexpected in drug therapy of osteoporosis, according to current art. Thus, the increase in bone turnover markers is inconsistent with the known anabolic effect of PTH to increase bone mass and strength, as shown by data in the present study.

The data from this 18 month study on cynomolgus monkeys supports the following unexpected findings:

Overall significant increase in total skeletal mass

Significant increase in bone mass and strength at the femur neck.

No evidence of "steal" from cortical bone to increase trabecular bone. Increase in bone mass and strength were statistically significant at sites enriched for either cortical bone (femur neck) or trabecular bone (lumbar vertebrae). At purely cortical bone sites (femur mid-diaphysis), there was a trend for PTH to stabilize or slightly increase bone mass and strength, compared to ovariectomized controls.

Changes in bone markers in ovariectomized monkeys (and humans) do not reflect the beneficial, anabolic effects of PTH on the skeleton. Use of body fluids from primates in the present study allows development of new and more valid surrogate markers.

Retention of the gain in bone mass and strength for at least 2 remodeling cycles after withdrawal of treatment.

This PTH primate study differs from published studies on rhesus and cynomolgus monkeys in that it used a large sample size to provide appropriate statistical power to detect differences that may not have been apparent in previous much smaller studies; controls included both ovariectomized primates (used in published studies) and sham operated, but intact primates. The latter control group has not been previously reported in this type of study, so that some of the benefits of PTH, and the restoration of certain measures to sham control levels, compared to values for ovariectomized animals were assessed for the first time.

Conclusions

This 18-month study in mature, feral, ovariectomized (OVX) cynomolgus monkeys, *Macaca fascicularis*, assured efficacy and safety in bone following treatment with rhPTH (1-34) for either 12 months followed by withdrawal of treatment for 6 months, or treatment for 18 months. rhPTH (1-34) significantly increased bone mass and strength of the spine and femur neck above ovariectomized controls to levels equivalent to or greater than those of sham controls. In ovariectomized monkeys treated with rhPTH(1-34), measures of calcium homeostatis (serum calcium, phosphate, and 1,25-dihydroxyvitamin D) were restored to that of sham controls. Serum, urine, and histomorphometry measures used to assess bone turnover showed rhPTH(1-34) maintained formation rates equivalent to or higher than those of ovariectomized controls, while biochemical markers of bone resorption remained equivalent to those of shame controls. In all animals treated with rhPTH(1-34) for up to 18 months, pharmacokinetic measures did not change with time, and there was no accumulation of rhPTH(1-34). There was no evidence of sustained hypercalcemia or kidney pathology after 18 months of treatment. There were no changes in mineralization or remodeling periods. The net gain in skeletal bone mineral content observed with rhPTH(1-34) may be explained by increased bone formation rate and bone forming surface with little or no effect on bone resorption. There were significant increases in bone mineral content, bone mineral density and biomechanical measures of strength, including toughness and stiffness, at clinically relevant sites such as the spine, femur neck and proximal tibia.

rhPTH(1-34) increased the rate of turnover in cortical bone of midshaft of the humerus and radius, but did not significantly alter bone mass or biomechanical measures of strength compared to either ovariectomized or sham controls. However, the increase in cortical width and/or cortical bone area is consistent with an increase in cross-sectional moment of inertia, a measure of strength and stiffness. rhPTH(1-34) had no significant effects on the intrinsic material properties of cortical bone. Endocortical bone formation was stimulated, thus increasing cortical width and intracortical porosity. It appears that these changes in porosity are responsible for maintaining the elasticity of the bone.

In monkeys, 12 months of treatment with rhPTH(1-34) followed by withdrawal for 6 months was associated with smaller, but still significant, gains in bone mass and strength in the spine and femur neck. Following withdrawal, no significant effects were noted on the cortical bone midshaft of the humerus and radius. Bone markers and histomorphometry showed trends to return to the low turnover values measured in sham controls.

In vivo mechanistic studies in rodents showed that genes associated with anabolic outcomes of rhPTH(1-34) are upregulated within 1 to 6 hours, and the increase in bone forming surfaces can be detected within 24 hours after the first dose in the absence of detectable effects on resorption. rhPTH(1-34) appears to recruit osteoprogenitors in S-phase, and stimulate their differentiation into osteoblasts, thereby rapidly increasing the percent bone forming surfaces. Single or multiple injections of rhPTH(1-34) may be given within a 1-hour period to induce the anabolic effect in bone. However, when the equivalent dose is given in young rats as multiple injections over 6 hours or 8 hours, the anabolic effect was abrogated, suggesting that brief, limited exposure to rhPTH(1-34) is required to induce the anabolic effect.

In summary, rhPTH(1-34) is anabolic on the bone in monkeys and rabbits, increasing bone mass and biomechanical strength measures at clinically relevant sites such as the lumbar spine and femur neck by selective stimulation of bone formation. The increases in bone turnover, endocortical surface formation, and porosity, detected by histomorphometry at cortical sites, did not alter bone mass or biomechanical measures of bone strength, but did increase the cross sectional moment of inertia by increasing cortical bone area and/or width, These studies demonstrate that administration of parathyroid hormone receptor activators, such as recombinant human PTH(1-34) improve bone quality both during and following treatment. In fact, administering PTH once daily for 18 months, or at the same doses for 12 months followed by a 6 month withdrawal phase, showed marked improvement of the quality of cortical bone of the humerus as analyzed by histomorphometry and polarized Fourier transform infrared (FTIR) microscopy. This analysis revealed that administration of PTH improved bone quality by replacing old bone (large crystallites) with young bone (range of sized crystallites, tending to smaller size). Thus, administration of PTH can increase cortical bone quality, improve mineralization, and accelerate mineralization and replacement of old bone by new bone.

Further, upon withdrawal of PTH from monkeys given low doses, there is an additional benefit as the matrix becomes more optimally mineralized, and the crystallites mature. That is, at low doses, PTH can have additional benefits during the withdrawal phase of treatment by enhancing mineralization. These data indicate benefits of a finite regime of treatment with PTH followed by a withdrawal period to achieve enhanced benefit. Current definitions of bone quality do not include these aspects of improved mineralization.

In earlier studies of a treatment phase of PTH followed by a phase of no treatment, the treatment phase was less than 1 month. The prolonged but finite treatment phase of 18-24 months followed by a period of at least 2 remodeling cycles has not previously been explored. The continued benefit in primates after withdrawal of treatment is in marked contrast to results achieved in rodents upon dosing with PTH. Studies of rats have uniformly shown that bone is rapidly lost following withdrawal of treatment. Gunness-Hey, M. and Hock, J. M. (1989) Bone 10: 447-452; Shen, V. et al. (1993) J. Clin Invest 91: 2479-2487; Shen, V. et al. (1992) Calcif Tissue Int. 50: 214-220; and Mosekilde, L. et al. (1997) Bone 20: 429-437.

Such a method of enhancing bone mineralization has not previously been observed and is unexpected, revealing a new method by which PTH strengthens and toughens bone and can prevent fractures. This new method includes enhancing and regulating mineralization, to provide tougher, stiffer, more fracture resistant bone. Such beneficial effects require more than new matrix formation. These findings indicate that PTH has benefits in patients with immobilized bones or skeletons, or in skeletons deficient in mineral, provided there is also adequate calcium and vitamin D supplementation.

Example 3

Increased Bone Strength and Density, and Reduced Fractures Upon Administration of rhPTH(1-34) to Humans Number of Subjects:
  rhPTH(1-34): 1093 enrolled, 848 finished.
  Placebo: 544 enrolled, 447 finished.
Diagnosis and Inclusion Criteria:
  Women ages 30 to 85 years, postmenopausal for a minimum of 5 years, with a minimum of one moderate or two mild atraumatic vertebral fractures.
Dosage and Administration:
  Test Product (blinded)
  rhPTH(1-34): 20 μg/day, given subcutaneously
  rhPTH(1-34): 40 μg/day, given subcutaneously
  Reference Therapy (blinded)
  Placebo study material for injection
Duration of Treatment:
  rhPTH(1-34): 17-23 months (excluding 6-month run-in phase)
  Placebo: 17-23 months (excluding 6-month run-in phase)
Criteria for Evaluation:
  Spine x-ray; serum biological markers (calcium, bone-specific alkaline phosphatase, procollagen I carboxy-terminal propeptide); urine markers (calcium, N-telopeptide, free deoxypyridinoline); 1,25-dihydroxyvitamin D; bone mineral density: spine, hip, wrist, and total body; height; population pharmacokinetic; bone biopsy (selected study sites).

|  | Placebo (N = 544) | PTH-20 (N = 541) | PTH-40 (N = 552) | p-value |
| --- | --- | --- | --- | --- |
| Caucasian | 98.9% | 98.9% | 98.4% | 0.672 |
| Age | 69.0 ± 7.0 | 69.5 ± 7.1 | 69.9 ± 6.8 | 0.099 |
| Years post menopausal | 20.9 ± 8.5 | 21.5 ± 8.7 | 21.8 ± 8.2 | 0.273 |
| Hysterectomized | 23.8% | 23.1% | 21.6% | 0.682 |
| Uterus + 0 or 1 ovary | 57 | 51 | 58 | |
| Uterus + 2 ovaries | 61 | 57 | 51 | |
| Unknown | 11 | 17 | 10 | |
| Previous osteoporosis drug use | 14.9% | 15.5% | 13.0% | 0.479 |
| Baseline spine BMD | 0.82 ± 0.17 | 0.82 ± 0.17 | 0.82 ± 0.17 | >0.990 |
| Baseline # of vert. fx | | | | >0.990 |
| 0 | 54 (10.4%) | 45 (8.8%) | 54 (10.1%) | |
| 1 | 144 (27.8%) | 159 (31.1%) | 16 (31.6%) | |
| 2 | 128 (24.7%) | 128 (25.0%) | 125 (23.4%) | |
| 3 | 75 (14.5%) | 67 (13.1%) | 81 (15.1%) | |
| 4 | 59 (11.4%) | 49 (9.6%) | 45 (8.4%) | |
| 5 | 28 (5.4%) | 31 (6.1%) | 21 (3.9%) | |
| 6 | 13 (2.5%) | 20 (3.9%) | 25 (4.7%) | |
| 7 | 6 (1.2%) | 7 (1.4%) | 10 (1.9%) | |
| 8 | 9 (1.7%) | 5 (1.0%) | 3 (0.6%) | |
| 9 | 1 (0.2%) | 0 | 2 (0.4%) | |
| 10 | 1 (0.2%) | 1 (0.2%) | 0 | |
| Unspecified | 26 | 29 | 17 | |

Results

Data from this clinical trial including a total of 1637 women treated with recombinant human parathyroid hormone (1-34), rhPTH(1-34)0, 20, or 40 μg/kg/day, and supplemented with vitamin D and calcium, for 18-24 months, showed results reported in Tables 15-19.

Table 15 illustrates data showing the reduction upon treatment with PTH of the number and severity of vertebral fractures. Comparing all PTH treated patients with placebo, the overall reduction in number of patients with vertebral fractures was 67% (p<0.001), with a 65% reduction (p<0.001) at 20 μg/day PTH compared to placebo, and a 69% reduction at 40 μg/day PTH compared to placebo (Table 15). Comparing all PTH treated patients with placebo, the overall reduction in number of patients with total number of fractures among the PTH treated patients compared to the placebo treated patients. The reduction is even more significant when considered as the reduction in the total number of fractures of hip, radius, ankle, humerus, ribs, foot, and pelvis among the PTH treated patients compared lo the placebo treated patients (Table 16).

TABLE 16

Effect of treatment with PTH on number of non-vertebral fractures.

| | Placebo | PTH-20 | PTH-40 | p-values | | | |
|---|---|---|---|---|---|---|---|
| | (N = 544) | (N = 541) | (N = 552) | Overall | PTH-pbo* | 20-pbo | 40-pbo |
| Hip | 4 | 2 | 3 | 0.718 | 0.474 | 0.417 | 0.690 |
| Radius | 13 | 7 | 10 | 0.404 | 0.236 | 0.180 | 0.504 |
| Ankle | 4 | 2 | 2 | 0.601 | 0.313 | 0.417 | 0.403 |
| Humerus | 5 | 4 | 3 | 0.767 | 0.534 | 0.744 | 0.465 |
| Ribs | 10 | 5 | 5 | 0.277 | 0.109 | 0.197 | 0.184 |
| Foot | 4 | 1 | 4 | 0.374 | 0.474 | 0.151 | 0.983 |
| Pelvis | 3 | 1 | 0 | 0.171 | 0.076 | 0.319 | 0.081 |
| Other | 16 | 14 | 9 | 0.338 | 0.296 | 0.723 | 0.146 |
| Total | 53 | 34 | 32 | 0.024 | 0.007 | 0.036 | 0.015 |
| Total w/o "Other" | 41 | 21 | 24 | 0.013 | 0.003 | 0.010 | 0.025 |

*Placebo (pbo)

multiple vertebral fractures was 81% (p<0.001), with a 77% reduction (p<0.001) at 20 μg/day PTH compared to placebo, and a 86% reduction at 40 μg/day PTH compared to placebo. Comparing all PTH treated patients with placebo, the overall reduction in number of patients with moderate to severe vertebral fractures was 84% (p<0.001), with a 90% reduction (p<0.001) at 20 μg/day PTH compared to placebo, and a 78% reduction at 40 μg/day PTH compared to placebo (Table 15).

TABLE 15

Effect of treatment with PTH on number and severity of vertebral fractures.

| | Placebo (n* = 448) | 20 μg/day PTH (n = 444) | 40 μg/day PTH (n = 434) |
|---|---|---|---|
| Number and percentage of patients with new vertebral fractures | 64 (14.3%) | 22 (5.0%) | 19 (4.4%) |
| Number and percentage of patients with 2 or more new vertebral fractures | 22 (4.9%) | 5 (1.1%) | 3 (0.7%) |
| Number and percentage of patients with new moderate to severe fractures** | 42 (9.4%) | 4 (0.9%) | 9 (2.1%) |

*n = number of patients with both baseline and endpoint x-rays
**Moderate fracture results in more than 25% loss of vertebral height (or an equivalent measure). Severe fracture results in more than 40% loss of vertebral height (or an equivalent measure). Fractures are as defined by Genant et al. (1993) Vertebral fracture assessment using a semiquantitative technique; J. Bone & Min Res 81137-1148.

Table 16 illustrates the effect of treatment with PTH on the number of fractures at various non-vertebral bones throughout the body. The number of fractures apparently decreased at each of the hip, radius, ankle, humerus, ribs, foot, pelvis, and other sites (Table 16). The reduction is statistically significant when viewed as the reduction in the The effect of PTH on bone mineral content (BMC), bone mineral density (BMD), and bone area were determined by dual energy absorptiometry (DEXA), and the results are reported in Tables 17-19. PTH administration caused apparent increases in BMC at the patient's lumbar spine, femur and hip, wrist, and throughout the patient's whole body (Table 17). Treatment with PTH caused significant increases in the patient's BMD at the lumbar spine, femur and hip (Table 18). The increases at the lumbar spine, femur and hip were statistically significant with p<0.001 (Table 18). Bone area apparently increased upon PTH treatment for the patient's lumbar spine, femur and hip (Table 19). The increases were statistically significant for the lumbar spine and hip neck (Table 19).

The effect of PTH on the whole body the measure of bone quantity and quality, BMC, is particularly significant. This whole body effect indicates that the amount of bone in the patient's body is increasing. PTH does not merely result in moving bone mass from one portion of the patient's body to another. Instead, treatment with PTH increases the amount and quality of bone in the patient's body.

Figure 9:
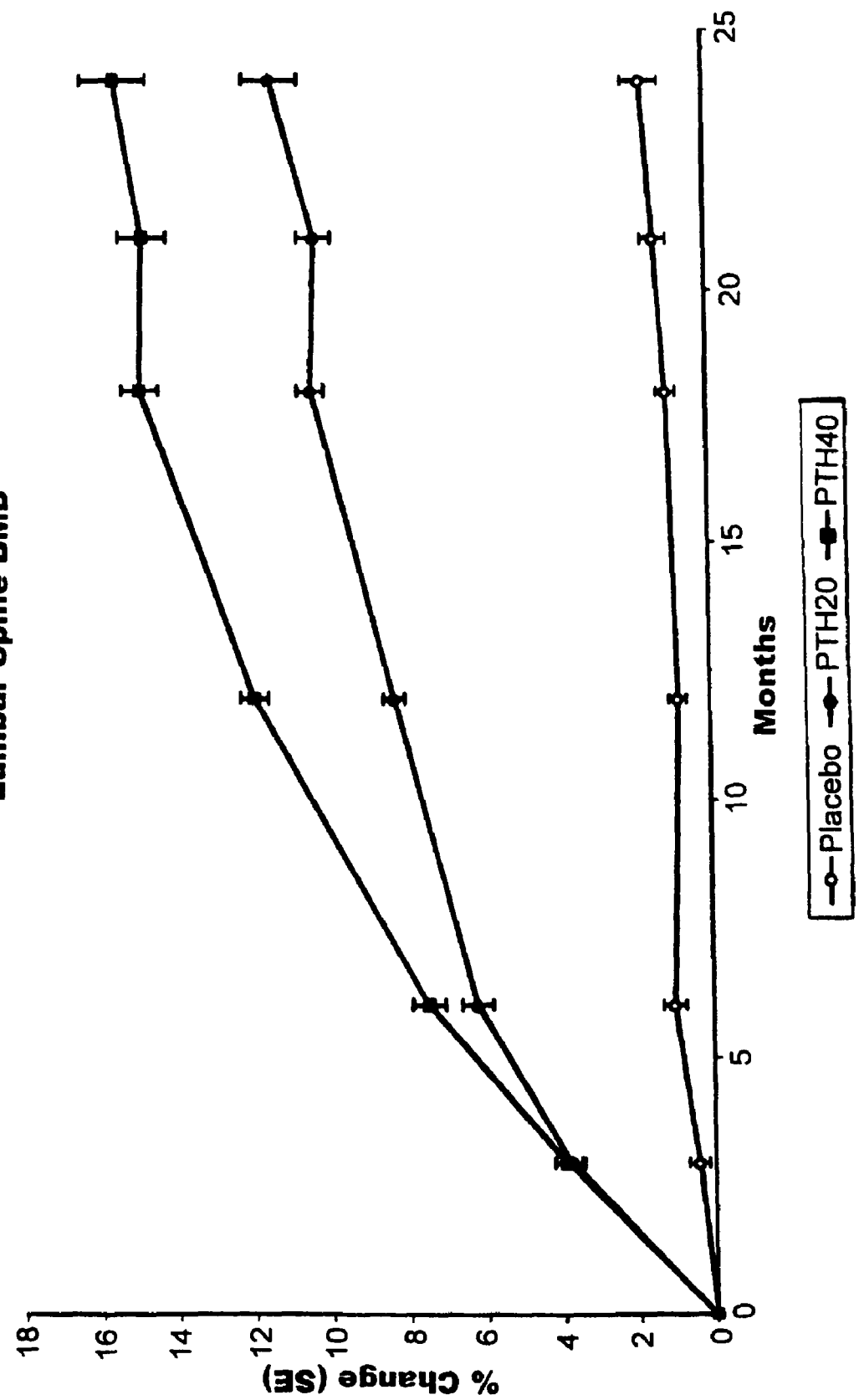
FIG. 9 illustrates increases in lumbar spine BMD through 23 months of treatment of patients with either 20 µg/kg/day PTH or 40 µg/kg/day PTH, compared to placebo treated controls.

FIGS. 9 and 10 illustrate the increases over time in lumbar spine BMD and femur/hip neck BMD, respectively, for PTH treated and placebo control patients. The patient's lumbar spine BMD increases steadily for at least about 18 months, with no or a less significant increase over the subsequent months. The patient's femur/hip BMD apparently increases for at least 18 months, and may increase upon further duration of PTH treatment.

TABLE 17

Effect of PTH on bone mineral content expressed as endpoint % change (SD) from baseline

| | Placebo | PTH-20 | PTH-40 | p-value |
|---|---|---|---|---|
| Lumbar spine | 1.60 (6.92) | 11.85 (8.83) | 16.62 (11.1) | <0.001 |

TABLE 17-continued

Effect of PTH on bone mineral content expressed as endpoint % change (SD) from baseline

| | Placebo | PTH-20 | PTH-40 | p-value |
|---|---|---|---|---|
| Femur/Hip | | | | |
| Total | −0.38 (5.18) | 3.50 (6.26) | 4.78 (6.70) | <0.001 |
| Neck | −0.51 (7.06) | 2.99 (7.26) | 5.80 (8.71) | <0.001 |
| Trochanter | 0.98 (14.97) | 5.68 (15.58) | 6.53 (15.33) | <0.001 |
| Intertrochanter | −0.23 (6.28) | 3.59 (7.32) | 4.99 (7.79) | <0.001 |
| Ward's triangle | 0.01 (14.75) | 5.36 (14.78) | 8.86 (17.02) | <0.001 |
| Wrist | | | | |
| Ultradistal | −1.67 (7.44) | −0.25 (6.53) | −1.88 (7.97) | 0.184 |
| ⅓ radius | −1.19 (6.12) | −1.37 (4.51) | −3.04 (6.09) | 0.025 |
| Whole body | −0.74 (4.76) | 1.30 (4.48) | 2.28 (5.44) | <0.001 |

TABLE 18

Effect of PTH on bone mineral density expressed as endpoint % change (SD) from baseline

| | Placebo | PTH-20 | PTH-40 | p-value |
|---|---|---|---|---|
| Lumbar spine | 1.13 (5.47) | 9.70 (7.41) | 13.7 (9.69) | <0.001 |
| Femur/Hip | | | | |
| Total | −1.01 (4.25) | 2.58 (4.88) | 3.60 (5.42) | <0.001 |
| Neck | −0.69 (5.39) | 2.79 (5.72) | 5.06 (6.73) | <0.001 |
| Trochanter | −0.21 (6.30) | 3.50 (6.81) | 4.40 (7.45) | <0.001 |
| Intertrochanter | −1.29 (4.53) | 2.62 (5.52) | 3.98 (5.96) | <0.001 |
| Ward's triangle | −0.80 (11.73) | 4.19 (11.93) | 7.85 (13.24) | <0.001 |
| Wrist | | | | |
| Ultradistal | −1.89 (7.98) | −0.05 (7.14) | −1.76 (7.20) | 0.108 |
| ⅓ radius | −1.22 (3.37) | −1.94 (4.07) | −3.17 (4.62) | 0.001 |

TABLE 19

Effect of PTH on bone area expressed as endpoint % change (SD) from baseline

| | Placebo | PTH-20 | PTH-40 | p-value |
|---|---|---|---|---|
| Lumbar spine | 0.46 (2.97) | 2.52 (3.52) | 3.34 (3.72) | <0.001 |
| Femur/Hip | | | | |
| Total | 0.54 (3.02) | 0.84 (3.16) | 1.05 (2.98) | 0.144 |
| Neck | 0.04 (4.60) | 0.27 (4.91) | 0.81 (5.56) | 0.035 |
| Trochanter | 0.95 (12.75) | 1.99 (12.16) | 1.92 (11.30) | 0.197 |
| Intertrochanter | 1.01 (5.17) | 1.01 (4.99) | 1.01 (4.89) | 0.964 |
| Ward's triangle | 0.44 (7.60) | 1.13 (7.34) | 0.99 (8.06) | 0.309 |
| Wrist | | | | |
| Ultradistal | 0.25 (6.40) | −0.25 (6.00) | −0.39 (4.80) | 0.653 |

TABLE 19-continued

Effect of PTH on bone area expressed as endpoint % change (SD) from baseline

| | Placebo | PTH-20 | PTH-40 | p-value |
|---|---|---|---|---|
| ⅓ radius | −0.02 (5.73) | 0.52 (3.40) | 0.01 (4.42) | 0.586 |

In summary, the data presented above indicate that patients treated with PTH have reduced fractures. Specifically, PTH treatment reduced by more than 66% the number of patients with prior vertebral fractures who suffered new vertebral fractures. PTH treatment also reduced by more than 78% the number of patients with prior vertebral fractures who suffered new, multiple vertebral fractures. In addition, PTH decreased the severity of vertebral fractures, with a significant reduction by 78% in the number of patients with moderate or severe fractures. Patients receiving PTH benefited from a significant reduction in all non-vertebral fractures (including fractures of hip, radius, wrist, pelvis, foot, humerus, ribs or ankle) with significance at a level of $p<0.007$. Bone quality increases as well. Patients with prior fracture benefited from a significant increase in bone mineral content of the hip, spine and total body. This increase indicates that fracture reduction at these sites can occur as early as after 12 months of therapy.

Discussion

These data on fractures are the first data on fracture reduction by PTH in humans. These findings demonstrate an improvement in bone quality and bone strength, like the preclinical data reported hereinabove. These results also show benefits in bone quality and strength at non-vertebral sites. The findings of a reduction in the numbers of fractures sustained during the 18-23 month period of treatment has not previously been observed in clinical or preclinical studies.

The question of whether PTH alone increases toughness and strength of bone to improve resistance to fracture has not previously been tested in humans. The published literature has consistently suggested that PTH must be given in combination with an anti-resorptive or estrogen. Previous, published clinical trials included patient populations too small to determine a significant reduction of fracture. In one study the benefits of PTH alone could not be assessed because there were no placebo controls. In a second study, employing the commonly accepted definition of fracture, no reduction in fracture was observed.

The findings of a reduction of fractures at combined non-vertebral sites is particularly unexpected in light of the common belief that PTH has negative effects at such sites. Common dogma holds that PTH will increase cortical porosity and therefore weaken bone, especially early in therapy. Further, this dogma asserts that cortical bone sites are at high risk of fracture and that PTH will offer no benefit in fracture reduction at non-vertebral sites. The dogma also holds that PTH alone is unlikely to be efficacious and will require concurrent anti-resorptive therapy to block negative effects on cortical bone. The present data demonstrate the previously unobserved benefits of PTH given to patients receiving vitamin D and calcium supplements. Unexpectedly, PTH strengthens bone to reduce the number of new fractures in a patient at risk for multiple fractures of the spine, at risk for additional non-vertebral fractures, at risk for moderate to severe additional fractures of the spine, and the like.

This clinical study on post-menopausal women showed particular benefits from treating patients with low dose (20 µg/day) since the dose of PTH (which, at high doses, could show side effects in some patients) was reduced, but fracture prevention and fracture reduction was retained, and similar to those noted at the high dose (40 µg/day). The FT-IR monkey data provide a possible, but not limiting, mechanistic explanation. The monkey study shows that low dose PTH increased crystal formation and accelerated mineralization in cortical bone. In addition, low dose monkeys showed additional benefits after withdrawal, as PTH enhanced mineral content of the bone. The present data demonstrate the novel finding that PTH given at low doses to patients receiving vitamin D and calcium supplements, is effective in preventing both vertebral and non-vertebral fractures. Contrary to popular belief, PTH strengthens bone at non-vertebral sites to prevent new fractures or reduce the severity of fractures, apparently by improving the mineralization and mineral content of the bone.

The invention has been described with reference to various specific and preferred embodiments and techniques. However, it should be understood that many variations and modifications may be made while remaining within the spirit and scope of the invention. All publications and patent applications in this specification are indicative of the level of ordinary skill in the art to which this invention pertains.

We claim:

1. A method for the treatment of a woman with osteoporosis and at risk for bone fracture comprising administering to said woman human parathyroid hormone (1-34) in a daily dose of 20 µg, without concurrent administration of an antiresorptive agent other than vitamin D or calcium, said treatment reducing the risk of vertebral and nonvertebral bone fracture.

2. The method of claim 1, wherein the osteoporosis is selected from advanced-stage osteoporosis, spinal osteoporosis, and steroid-induced osteoporosis.

3. A method for the treatment of a man with osteoporosis and at risk for bone fracture comprising administering to said man human parathyroid hormone (1-34) in a daily dose of 20 µg, without concurrent administration of an antiresorptive agent other than vitamin D or calcium, said treatment reducing the risk of vertebral and non-vertebral bone fracture.

4. The method of claim 3 in which said man has hypogonadal osteoporosis.

* * * * *